(12) United States Patent
Zbiljic

(10) Patent No.: US 11,558,487 B2
(45) Date of Patent: *Jan. 17, 2023

(54) METHODS AND SYSTEMS FOR STREAM-PROCESSING OF BIOMEDICAL DATA

(71) Applicant: Seven Bridges Genomics Inc., Charlestown, MA (US)

(72) Inventor: Nemanja Zbiljic, Belgrade (RS)

(73) Assignee: SEVEN BRIDGES GENOMICS INC., Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/191,187

(22) Filed: Mar. 3, 2021

(65) Prior Publication Data

US 2021/0258399 A1  Aug. 19, 2021

Related U.S. Application Data

(63) Continuation of application No. 15/497,524, filed on Apr. 26, 2017, now Pat. No. 10,972,574.

(Continued)

(51) Int. Cl.
| | |
|---|---|
| *H04L 67/5681* | (2022.01) |
| *G06F 16/182* | (2019.01) |
| *G06F 12/0862* | (2016.01) |
| *G16B 50/00* | (2019.01) |
| *G06F 12/02* | (2006.01) |

(Continued)

(52) U.S. Cl.
CPC ...... *H04L 67/5681* (2022.05); *G06F 12/0246* (2013.01); *G06F 12/0862* (2013.01); *G06F 16/1827* (2019.01); *G16B 50/00* (2019.02); *G16B 50/30* (2019.02); *H04L 67/1097* (2013.01); *G06F 12/02* (2013.01); *G06F 2212/1021* (2013.01); *G06F 2212/6026* (2013.01); *H04L 65/80* (2013.01)

(58) Field of Classification Search
CPC ... H04L 65/60; H04L 65/608; H04L 67/2847; H04L 67/1014; H04L 29/0809
See application file for complete search history.

(56) References Cited

U.S. PATENT DOCUMENTS

| | | | | |
|---|---|---|---|---|
| 9,710,386 | B1 * | 7/2017 | Zhang | G06F 12/00 |
| 2003/0225977 | A1 * | 12/2003 | Desai | G06F 3/0601 |
| | | | | 711/137 |

(Continued)

*Primary Examiner* — Barbara B Anyan
(74) *Attorney, Agent, or Firm* — Blueshift IP, LLC; Cynthia Gilbert

(57) ABSTRACT

A method for stream-processing biomedical data includes receiving, by a file system on a computing device, a first request for access to at least a first portion of a file stored on a remotely located storage device. The method includes receiving, by the file system, a second request for access to at least a second portion of the file. The method includes determining, by a pre-fetching component executing on the computing device, whether the first request and the second request are associated with a sequential read operation. The method includes automatically retrieving, by the pre-fetching component, a third portion of the requested file, before receiving a third request for access to least the third portion of the file, based on a determination that the first request and the second request are associated with the sequential read operation.

18 Claims, 7 Drawing Sheets

Related U.S. Application Data

(60) Provisional application No. 62/328,381, filed on Apr. 27, 2016.

(51) Int. Cl.
  *G16B 50/30* (2019.01)
  *H04L 67/1097* (2022.01)
  *H04L 65/80* (2022.01)

(56) References Cited

U.S. PATENT DOCUMENTS

| | | | | |
|---|---|---|---|---|
| 2005/0253858 | A1* | 11/2005 | Ohkami | G06F 12/0862 |
| | | | | 345/531 |
| 2007/0214325 | A1* | 9/2007 | Sasamoto | G06F 12/0862 |
| | | | | 711/137 |
| 2009/0089501 | A1* | 4/2009 | Ahn | G06F 12/0862 |
| | | | | 711/113 |
| 2013/0097309 | A1* | 4/2013 | Ma | H04L 67/2847 |
| | | | | 709/224 |
| 2013/0179632 | A1* | 7/2013 | Ben-Shemesh | G06F 12/0862 |
| | | | | 711/105 |
| 2016/0007057 | A1* | 1/2016 | Niesen | H04N 21/23106 |
| | | | | 725/115 |
| 2016/0182582 | A1* | 6/2016 | Wagenaar | H04L 65/608 |
| | | | | 709/231 |
| 2016/0241913 | A1* | 8/2016 | Bhandari | H04L 65/80 |
| 2017/0031823 | A1* | 2/2017 | Ross | G06F 12/0862 |
| 2017/0054800 | A1* | 2/2017 | DiVincenzo | H04N 21/2187 |
| 2017/0123988 | A1* | 5/2017 | Chun | G06F 12/0862 |
| 2017/0185520 | A1* | 6/2017 | Matsuo | G06F 12/0862 |

* cited by examiner

METHODS AND SYSTEMS FOR STREAM-PROCESSING OF BIOMEDICAL DATA

CROSS-REFERENCE TO RELATED APPLICATIONS

This application is a continuation of U.S. Nonprovisional patent application Ser. No. 15/497,524, filed on Apr. 26, 2017, entitled "Methods and Systems for Stream-Processing of Biomedical Data", which application claims priority from U.S. Provisional Patent Application Ser. No. 62/328,381, filed on Apr. 27, 2016, entitled "Methods and Systems for Stream-Processing of Biomedical Data," each of which is hereby incorporated by reference.

BACKGROUND

The disclosure relates to data processing. More particularly, the methods and systems described herein relate to functionality for stream-processing biomedical data sets.

A conventional model for genomic data analysis typically requires downloading large data sets, incorporating new locally generated data, and then performing computational analyses on this data using local hardware. This model has been successfully employed by researchers for many years, but has recently presented a bottleneck, given the enormous growth in the size of biomedical data sets. Large-scale scientific programs using next-generation sequencing technology, such as the 1000 Genomes Project, the Human Microbiome Project (HMP), and The Cancer Genome Atlas (TCGA), have grown to a point in which it is impractical for individual researchers to download, store, and analyze common genomic data sets. For example, the full size of the TCGA data set is expected to exceed over 2.5 Petabytes of data. Few researchers have this level of storage capacity, and for those who do, simply downloading this amount of data could take months over a conventional network connection.

Cloud computing offers one solution to these issues; that is, the implementation of an infrastructure architecture in which one or more networks owned, managed, or otherwise associated with a first entity provide computing infrastructure on behalf of a customer that is, conventionally, associated with a separate entity. By co-locating bioinformatics analysis tools with genomic data sets on cloud computing resources, individual researchers can perform analyses without having to purchase expensive hardware or transfer large files back and forth. However, creating an effective, large-scale cloud infrastructure for genomics and clinical data is challenging. Next-generation sequencing produces millions to billions of sequence fragments read from longer DNA molecules present in a particular sample (i.e., "sequence reads"), usually of short length—e.g., 50-200 pairs of complementary bases in a double-stranded nucleic acid molecule ("base pairs"). Sequence reads and other genomic data sets are often processed sequentially (e.g., in order to map or align the fragments to one or more sections of a reference genome). However, in conventional systems for processing such data, an entire data set is copied to a local instance (e.g., a locally-instantiated virtual machine, such as an instance provided by Amazon Web Services, Inc.) from backing storage (e.g., a remotely located server providing one or more units of storage, such as an "S3 bucket" provided by Amazon Web Services, Inc.) before a job can begin. Similarly, once a job has completed, the resulting output is often transferred back to the backing storage. This is further complicated by the fact that many genomics analyses are so large that they exceed the local storage available on a compute instance.

Network file systems (such as NFS) exist, but typically are not able to efficiently handle the combination of latency and file sizes associated with cloud computing and next generation sequencing. While downloading an entire file locally may improve performance, bulky upload and download applications can complicate a particular workflow. Similarly, conventional methods of processing data as the data is streamed from a remote computing device to a local computing device, do not typically provide functionality for the types of processing applied to biomedical data, which are often more sophisticated and computationally intense processing types than that applied to streams of other types of data.

BRIEF SUMMARY

In one aspect, a method for stream-processing biomedical data includes receiving, by a file system on a computing device, a first request for access to at least a first portion of a file stored on a remotely located storage device. The method includes receiving, by the file system, a second request for access to at least a second portion of the file. The method includes determining, by a pre-fetching component executing on the computing device, whether the first request and the second request are associated with a sequential read operation. The method includes automatically retrieving, by the pre-fetching component, a third portion of the requested file, before receiving a third request for access to least the third portion of the file, based on a determination that the first request and the second request are associated with the sequential read operation.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

In some embodiments, the methods and systems described herein provide functionality for stream-processing biomedical data. Before describing these methods and systems in detail, however, a description is provided of a network in which such methods and systems may be implemented.

Figure 1A:
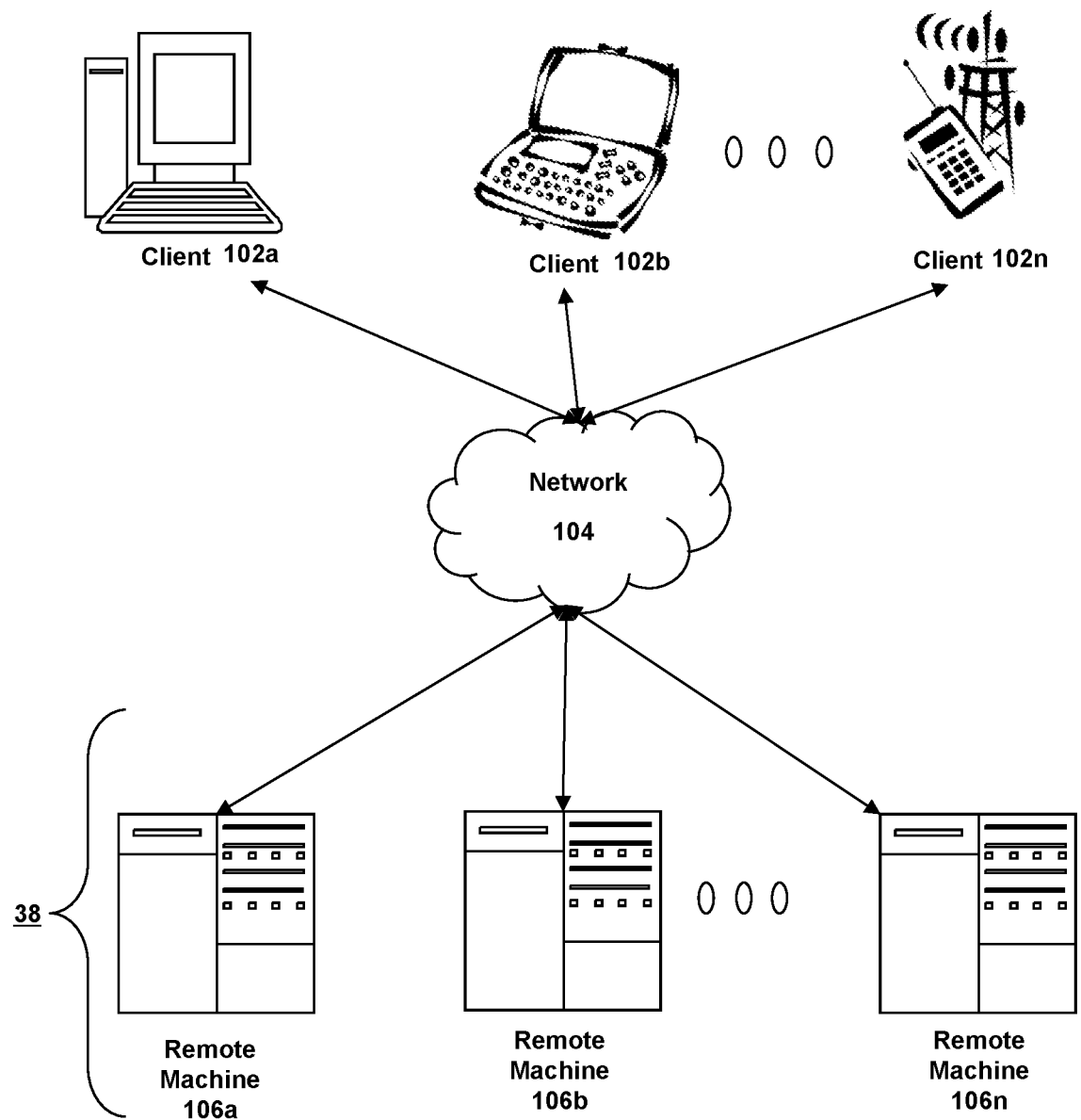
FIGS. 1A-1C are block diagrams depicting embodiments of computers useful in connection with the methods and systems described herein.

Referring now to FIG. 1A, an embodiment of a network environment is depicted. In brief overview, the network environment comprises one or more clients 102a-102n (also generally referred to as local machine(s) 102, client(s) 102, client node(s) 102, client machine(s) 102, client computer(s)

102, client device(s) 102, computing device(s) 102, endpoint(s) 102, or endpoint node(s) 102) in communication with one or more remote machines 106a-106n (also generally referred to as server(s) 106 or computing device(s) 106) via one or more networks 104.

Although FIG. 1A shows a network 104 between the clients 102 and the remote machines 106, the clients 102 and the remote machines 106 may be on the same network 104. The network 104 can be a local area network (LAN), such as a company Intranet, a metropolitan area network (MAN), or a wide area network (WAN), such as the Internet or the World Wide Web. In some embodiments, there are multiple networks 104 between the clients 102 and the remote machines 106. In one of these embodiments, a network 104' (not shown) may be a private network and a network 104 may be a public network. In another of these embodiments, a network 104 may be a private network and a network 104' a public network. In still another embodiment, networks 104 and 104' may both be private networks.

The network 104 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. In some embodiments, the network 104 may comprise a wireless link, such as an infrared channel or satellite band. The topology of the network 104 may be a bus, star, or ring network topology. The network 104 may be of any such network topology as known to those ordinarily skilled in the art capable of supporting the operations described herein. The network may comprise mobile telephone networks utilizing any protocol or protocols used to communicate among mobile devices (including tables and handheld devices generally), including AMPS, TDMA, CDMA, GSM, GPRS, UMTS, or LTE. In some embodiments, different types of data may be transmitted via different protocols. In other embodiments, the same types of data may be transmitted via different protocols.

A client 102 and a remote machine 106 (referred to generally as computing devices 100) can be any workstation, desktop computer, laptop or notebook computer, server, portable computer, mobile telephone, mobile smartphone, or other portable telecommunication device, media playing device, a gaming system, mobile computing device, or any other type and/or form of computing, telecommunications or media device that is capable of communicating on any type and form of network and that has sufficient processor power and memory capacity to perform the operations described herein. A client 102 may execute, operate or otherwise provide an application, which can be any type and/or form of software, program, or executable instructions, including, without limitation, any type and/or form of web browser, web-based client, client-server application, an ActiveX control, or a JAVA applet, or any other type and/or form of executable instructions capable of executing on client 102.

In one embodiment, a computing device 106 provides the functionality of a web server. In some embodiments, a web server 106 comprises an open-source web server, such as the APACHE servers maintained by the Apache Software Foundation of Delaware. In other embodiments, the web server executes proprietary software, such as the INTERNET INFORMATION SERVICES products provided by Microsoft Corporation of Redmond, Wash., the ORACLE IPLANET web server products provided by Oracle Corporation of Redwood Shores, Calif., or the BEA WEBLOGIC products provided by BEA Systems of Santa Clara, Calif.

In some embodiments, the system may include multiple, logically-grouped remote machines 106. In one of these embodiments, the logical group of remote machines may be referred to as a server farm 38. In another of these embodiments, the server farm 38 may be administered as a single entity.

Figure 1B:
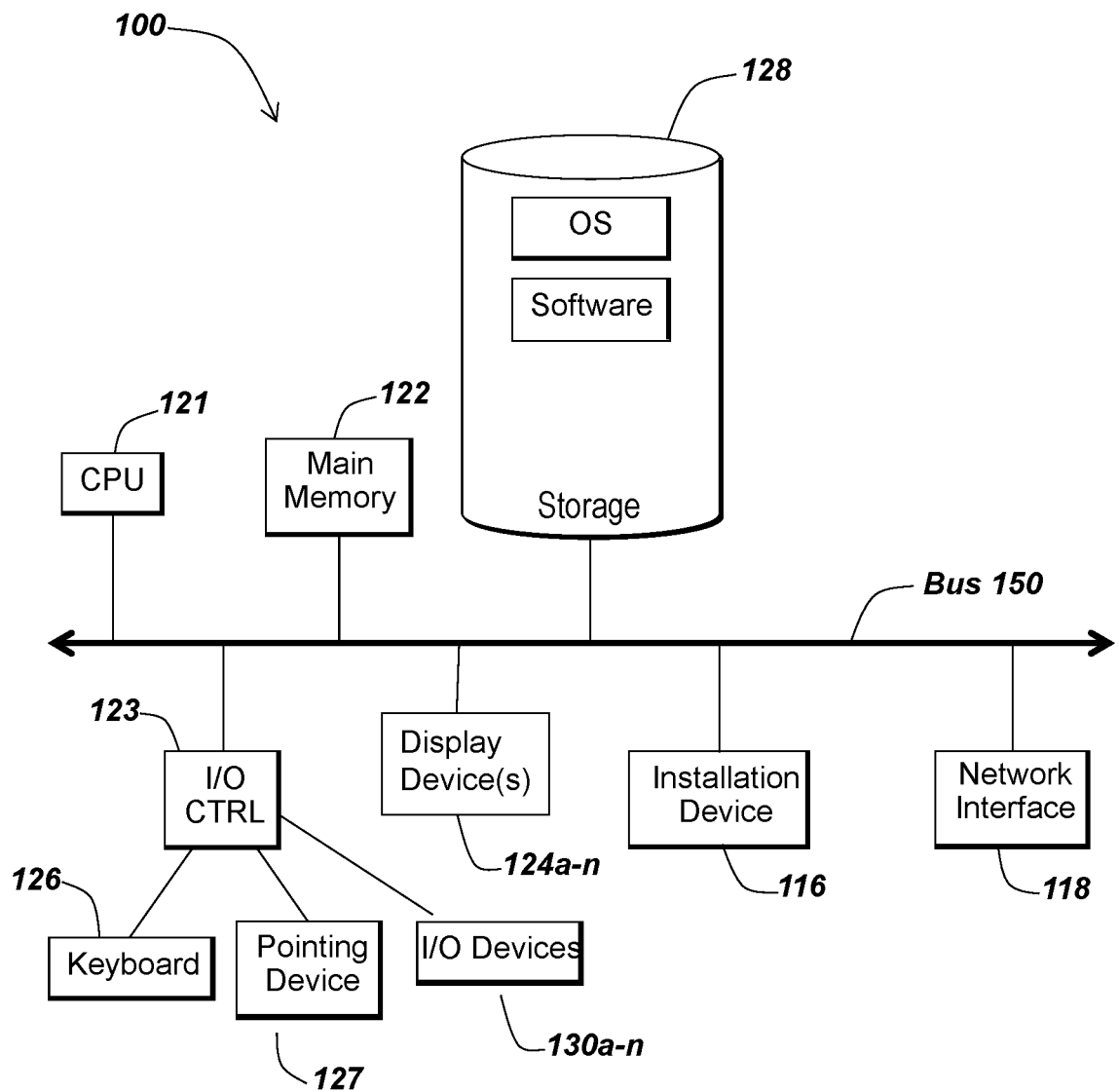
Figure 1C:
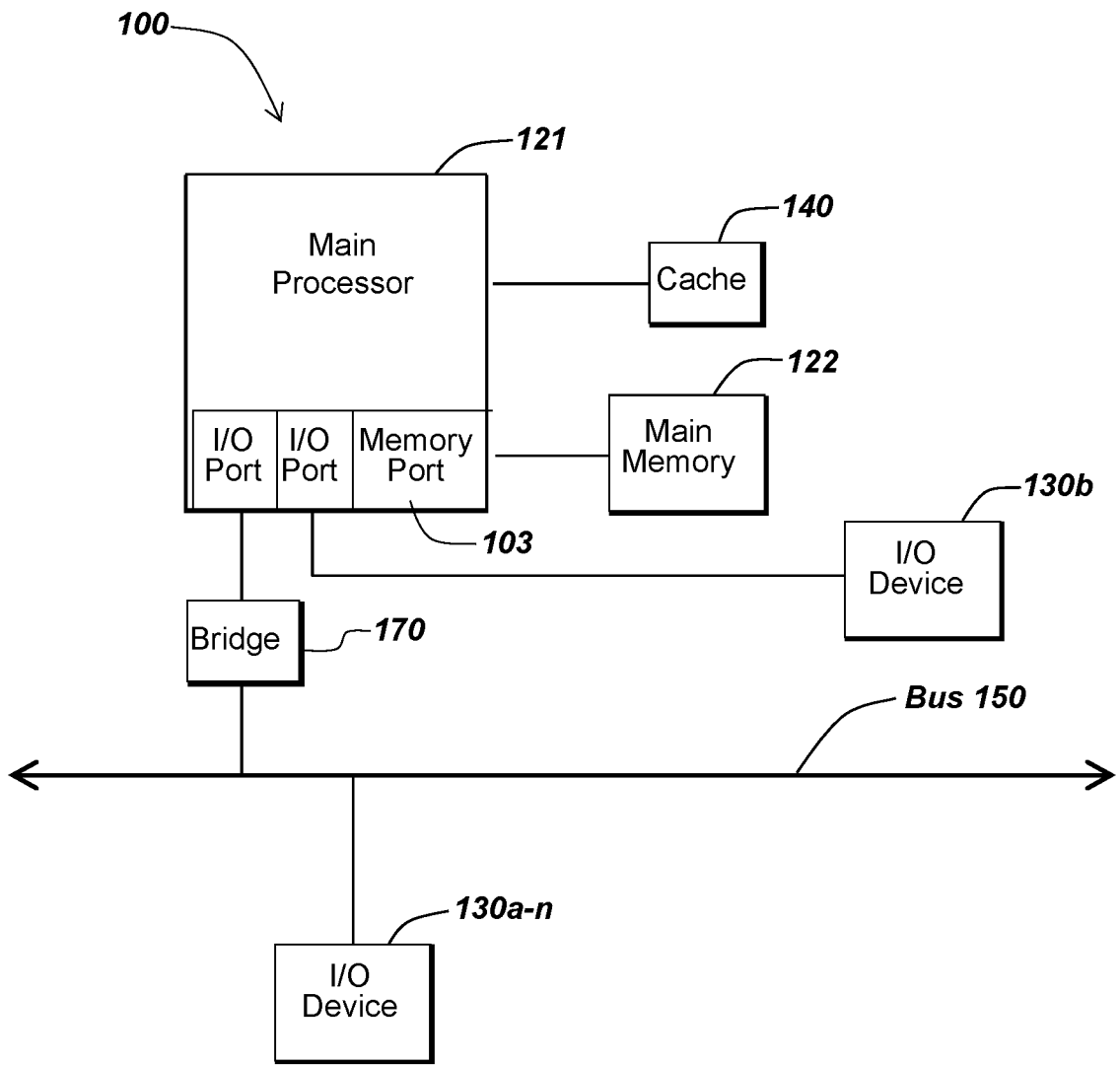

FIGS. 1B and 1C depict block diagrams of a computing device 100 useful for practicing an embodiment of the client 102 or a remote machine 106. As shown in FIGS. 1B and 1C, each computing device 100 includes a central processing unit 121, and a main memory unit 122. As shown in FIG. 1B, a computing device 100 may include a storage device 128, an installation device 116, a network interface 118, an I/O controller 123, display devices 124a-n, a keyboard 126, a pointing device 127, such as a mouse, and one or more other I/O devices 130a-n. The storage device 128 may include, without limitation, an operating system and software. As shown in FIG. 1C, each computing device 100 may also include additional optional elements, such as a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, such as: those manufactured by Intel Corporation of Mountain View, Calif.; those manufactured by Motorola Corporation of Schaumburg, Ill.; those manufactured by Transmeta Corporation of Santa Clara, Calif.; those manufactured by International Business Machines of White Plains, N.Y.; or those manufactured by Advanced Micro Devices of Sunnyvale, Calif. Other examples include SPARC processors, ARM processors, processors used to build UNIX/LINUX "white" boxes, and processors for mobile devices. The computing device 100 may be based on any of these processors, or any other processor capable of operating as described herein.

Main memory unit 122 may be one or more memory chips capable of storing data and allowing any storage location to be directly accessed by the microprocessor 121. The main memory 122 may be based on any available memory chips capable of operating as described herein. In the embodiment shown in FIG. 1B, the processor 121 communicates with main memory 122 via a system bus 150. FIG. 1C depicts an embodiment of a computing device 100 in which the processor communicates directly with main memory 122 via a memory port 103. FIG. 1C also depicts an embodiment in which the main processor 121 communicates directly with cache memory 140 via a secondary bus, sometimes referred to as a backside bus. In other embodiments, the main processor 121 communicates with cache memory 140 using the system bus 150.

In the embodiment shown in FIG. 1B, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1C depicts an embodiment of a computer 100 in which the main processor 121 also communicates directly with an I/O device 130b via, for example, HYPERTRANSPORT, RAPIDIO, or INFINI-BAND communications technology.

A wide variety of I/O devices 130a-130n may be present in the computing device 100. Input devices include keyboards, mice, trackpads, trackballs, microphones, scanners, cameras, and drawing tablets. Output devices include video displays, speakers, inkjet printers, laser printers, and dye-sublimation printers. The I/O devices may be controlled by an I/O controller 123 as shown in FIG. 1B. Furthermore, an I/O device may also provide storage and/or an installation medium 116 for the computing device 100. In some embodiments, the computing device 100 may provide USB connections (not shown) to receive handheld USB storage devices such as the USB Flash Drive line of devices manufactured by Twintech Industry, Inc. of Los Alamitos, Calif.

Referring still to FIG. 1B, the computing device 100 may support any suitable installation device 116, such as a floppy disk drive for receiving floppy disks such as 3.5-inch, 5.25-inch disks or ZIP disks; a CD-ROM drive; a CD-R/RW drive; a DVD-ROM drive; tape drives of various formats; a USB device; a hard-drive or any other device suitable for installing software and programs. In some embodiments, the computing device 100 may provide functionality for installing software over a network 104. The computing device 100 may further comprise a storage device, such as one or more hard disk drives or redundant arrays of independent disks, for storing an operating system and other software. Alternatively, the computing device 100 may rely on memory chips for storage instead of hard disks.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, 802.15.4, Bluetooth, ZIGBEE, CDMA, GSM, WiMax, and direct asynchronous connections). In one embodiment, the computing device 100 communicates with other computing devices 100' via any type and/or form of gateway or tunneling protocol such as Secure Socket Layer (SSL) or Transport Layer Security (TLS). The network interface 118 may comprise a built-in network adapter, network interface card, PCMCIA network card, card bus network adapter, wireless network adapter, USB network adapter, modem, or any other device suitable for interfacing the computing device 100 to any type of network capable of communication and performing the operations described herein.

In some embodiments, the computing device 100 may comprise or be connected to multiple display devices 124a-124n, each of which may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. One ordinarily skilled in the art will recognize and appreciate the various ways and embodiments that a computing device 100 may be configured to have multiple display devices 124a-124n.

In further embodiments, an I/O device 130 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

A computing device 100 of the sort depicted in FIGS. 1B and 1C typically operates under the control of operating systems, which control scheduling of tasks and access to system resources. The computing device 100 can be running any operating system such as any of the versions of the MICROSOFT WINDOWS operating systems, the different releases of the UNIX and LINUX operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS CE, WINDOWS XP, WINDOWS 7, WINDOWS 8, and WINDOWS VISTA, all of which are manufactured by Microsoft Corporation of Redmond, Wash.; MAC OS manufactured by Apple Inc. of Cupertino, Calif.; OS/2 manufactured by International Business Machines of Armonk, N.Y.; Red Hat Enterprise Linux, a Linus-variant operating system distributed by Red Hat, Inc., of Raleigh, N.C.; Ubuntu, a freely-available operating system distributed by Canonical Ltd. of London, England; or any type and/or form of a Unix operating system, among others.

The computing device 100 can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein. In some embodiments, the computing device 100 may have different processors, operating systems, and input devices consistent with the device. In other embodiments, the computing device 100 is a mobile device, such as a JAVA-enabled cellular telephone/smartphone or personal digital assistant (PDA). The computing device 100 may be a mobile device such as those manufactured, by way of example and without limitation, by Apple Inc. of Cupertino, Calif.; Google/Motorola Div. of Ft. Worth, Tex.; Kyocera of Kyoto, Japan; Samsung Electronics Co., Ltd. of Seoul, Korea; Nokia of Finland; Hewlett-Packard Development Company, L.P. and/or Palm, Inc. of Sunnyvale, Calif.; Sony Ericsson Mobile Communications AB of Lund, Sweden; or Research In Motion Limited of Waterloo, Ontario, Canada. In yet other embodiments, the computing device 100 is a smartphone, POCKET PC, POCKET PC PHONE, or other portable mobile device supporting Microsoft Windows Mobile Software.

In some embodiments, the computing device 100 is a digital audio player. In one of these embodiments, the computing device 100 is a digital audio player such as the Apple IPOD, IPOD TOUCH, IPOD NANO, and IPOD SHUFFLE lines of devices manufactured by Apple Inc. In another of these embodiments, the digital audio player may function as both a portable media player and as a mass storage device. In other embodiments, the computing device 100 is a digital audio player such as those manufactured by, for example, and without limitation, Samsung Electronics America of Ridgefield Park, N.J., or Creative Technologies Ltd. of Singapore. In yet other embodiments, the computing device 100 is a portable media player or digital audio player supporting file formats including, but not limited to, MP3, WAV, M4A/AAC, WMA Protected AAC, AEFF, Audible audiobook, Apple Lossless audio file formats, and .mov, .m4v, and .mp4 MPEG-4 (H.264/MPEG-4 AVC) video file formats.

In some embodiments, the computing device 100 comprises a combination of devices, such as a mobile phone combined with a digital audio player or portable media player. In one of these embodiments, the computing device 100 is a device in the Google/Motorola line of combination digital audio players and mobile phones. In another of these embodiments, the computing device 100 is a device in the IPHONE smartphone line of devices manufactured by Apple Inc. In still another of these embodiments, the computing device 100 is a device executing the ANDROID open source mobile phone platform distributed by the Open Handset Alliance; for example, the device 100 may be a device such as those provided by Samsung Electronics of Seoul, Korea, or HTC Headquarters of Taiwan, R.O.C. In other embodiments, the computing device 100 is a tablet device such as, for example and without limitation, the IPAD line of devices manufactured by Apple Inc.; the PLAYBOOK manufactured by Research In Motion; the CRUZ line of devices manufactured by Velocity Micro, Inc. of Richmond, Va.; the FOLIO and THRIVE line of devices manufactured by Toshiba America Information Systems, Inc. of Irvine, Calif.; the GALAXY line of devices manufactured by Samsung; the HP SLATE line of devices manufactured by Hewlett-Packard; and the STREAK line of devices manufactured by Dell, Inc. of Round Rock, Tex.

Figure 1D:
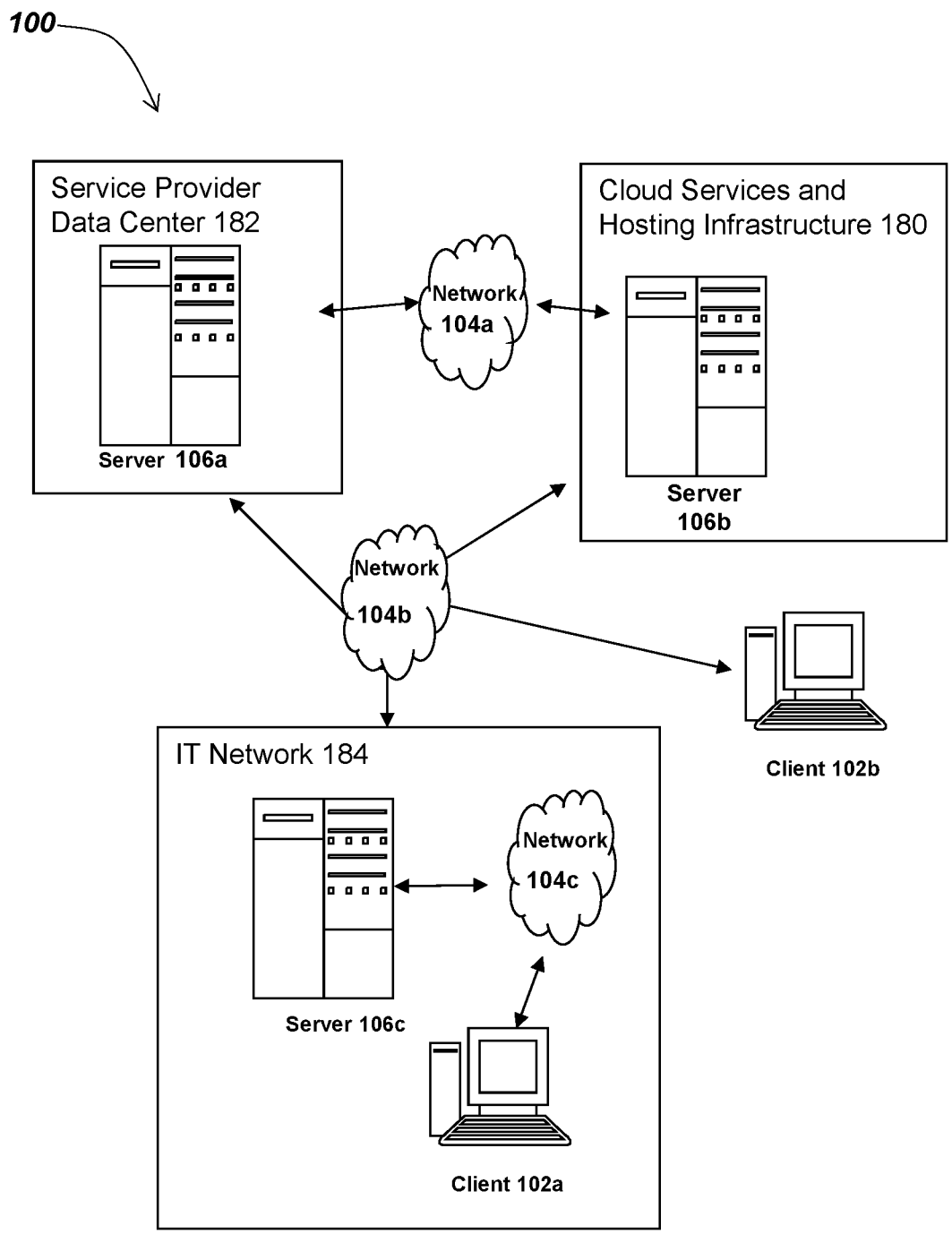
FIG. 1D is a block diagram depicting one embodiment of a system in which a plurality of networks provides data hosting and delivery services.

Referring now to FIG. 1D, a block diagram depicts one embodiment of a system in which a plurality of networks provides hosting and delivery services. In brief overview, the system includes a cloud services and hosting infrastructure 180, a service provider data center 182, and an information technology (IT) network 184.

In one embodiment, the data center 182 includes computing devices such as, without limitation, servers (including, for example, application servers, file servers, databases, and backup servers), routers, switches, and telecommunications equipment. In another embodiment, the cloud services and hosting infrastructure 180 provides access to, without limitation, storage systems, databases, application servers, desktop servers, directory services, web servers, as well as services for accessing remotely located hardware and software platforms. In still other embodiments, the cloud services and hosting infrastructure 180 includes a data center 182. In other embodiments, however, the data center 182 relies on services provided by a third-party cloud services and hosting infrastructure 180.

In some embodiments, the IT network 104c may provide local services, such as mail services and web services. In other embodiments, the IT network 104c may provide local versions of remotely located services, such as locally-cached versions of remotely-located print servers, databases, application servers, desktop servers, directory services, and web servers. In further embodiments, additional servers may reside in the cloud services and hosting infrastructure 180, the data center 182, or other networks altogether, such as those provided by third-party service providers including, without limitation, infrastructure service providers, application service providers, platform service providers, tools service providers, web site hosting services, and desktop service providers.

In one embodiment, a user of a client 102 accesses services provided by a remotely located server 106a. For instance, an administrator of an enterprise IT network 184 may determine that a user of the client 102a will access an application executing on a virtual machine executing on a remote server 106a. As another example, an individual user of a client 102b may use a resource provided to consumers by the remotely located server 106 (such as email, fax, voice or other communications service, data backup services, or other service).

As depicted in FIG. 1D, the data center 182 and the cloud services and hosting infrastructure 180 are remotely located from an individual or organization supported by the data center 182 and the cloud services and hosting infrastructure 180; for example, the data center 182 may reside on a first network 104a and the cloud services and hosting infrastructure 180 may reside on a second network 104b, while the IT network 184 is a separate, third network 104c. In other embodiments, the data center 182 and the cloud services and hosting infrastructure 180 reside on a first network 104a and the IT network 184 is a separate, second network 104c. In still other embodiments, the cloud services and hosting infrastructure 180 resides on a first network 104a while the data center 182 and the IT network 184 form a second network 104c. Although FIG. 1D depicts only one sever 106a, one server 106b, one server 106c, two clients 102, and three networks 104, it should be understood that the system may provide multiple ones of any or each of those components. The servers 106, clients 102, and networks 104 may be provided as described above in connection with FIGS. 1A-1C.

Therefore, in some embodiments, an IT infrastructure may extend from a first network—such as a network owned and managed by an individual or an enterprise—into a second network, which may be owned or managed by a separate entity than the entity owning or managing the first network. Resources provided by the second network may be said to be "in a cloud." Cloud-resident elements may include, without limitation, storage devices, servers, databases, computing environments (including virtual machines, servers, and desktops), and applications. For example, the IT network 184 may use a remotely located data center 182 to store servers (including, for example, application servers, file servers, databases, and backup servers), routers, switches, and telecommunications equipment. As another example, the cloud-resident elements may include mountable storage such as, without limitation, an AMAZON Elastic Block Storage (EBS) provided by Amazon Web Services, Inc. of Seattle, Wash. The data center 182 may be owned and managed by the IT network 184 or a third-party service provider (including for example, a cloud services and hosting infrastructure provider) may provide access to a separate data center 182.

In some embodiments, one or more networks providing computing infrastructure on behalf of customers is referred to as a cloud. In one of these embodiments, a system in which users of a first network access at least a second network including a pool of abstracted, scalable, and managed computing resources capable of hosting resources may be referred to as a cloud computing environment. In another of these embodiments, resources may include, without limitation, virtualization technology, data center resources, applications, and management tools. In some embodiments, Internet-based applications (which may be provided via a "software-as-a-service" model) may be referred to as cloud-based resources. In other embodiments, networks that provide users with computing resources, such as remote servers, virtual machines, or blades on blade servers, may be referred to as compute clouds or "infrastructure-as-a-service" providers. In still other embodiments, networks that provide storage resources, such as storage area networks, may be referred to as storage clouds. In further embodiments, a resource may be cached in a local network and stored in a cloud.

In some embodiments, some or all of a plurality of remote machines 106 may be leased or rented from third-party companies such as, by way of example and without limitation, Amazon Web Services, Inc.; Rackspace US, Inc. of San Antonio, Tex.; Microsoft Corporation of Redmond, Wash.; and Google Inc. of Mountain View, Calif. In other embodiments, all the hosts 106 are owned and managed by third-party companies including, without limitation, Amazon Web Services, Inc., Rackspace US, Inc., Microsoft Corporation, and Google Inc.

Computing resources generally may include, without limitation, physical or virtualized computing components that users' machines 100 may access directly or over a network 104. For example, and without limitation, the computing resources may include computers 100 as described above in connection with FIGS. 1A-1D. By way of further example, the computing resources may include physical computers, virtual computers, virtual computer components (such as hard drives), physical computers (including, by way of example, blades on blade servers or other types of shared or dedicated servers), memory, network devices, databases, input/output systems, operating system software, application software, or any type of software. In other embodiments, the computing resources act as intermediaries and provide access to other remote machines. For example, a first computing resource may provide access to a second machine 106b that executes software made available over the network 104; by way of example, a software-as-a-service provider may execute software on a second machine 106b that a user can access via the first computing resource.

Conventional bioinformatics tools typically rely on sequential reading and writing. One of ordinary skill in the art would understand the phrase "sequential reading" to refer to the accessing of data files in a predetermined, ordered sequence. This is in contrast to random access, in which data files are read or written in any order without the need to pass through all intervening points. Sequential access is much faster than random access, as the latter requires a higher number of seek operations. This speed is critical when processing biomedical data files, which are often extremely large (upwards of hundreds of gigabytes, for example). Traditional methods of processing large biomedical data files require that the entire files are loaded into computer memory, which would require a prohibitively large amount of Random Access Memory (RAM). Furthermore, outputs of analyses performed on these data files can be similarly large, in which case sequential writing of output files can be utilized.

Processing a data file sequentially (e.g., line by line) is also important when processing biomedical data because bioinformatics tools typically process or transform data files from one format into another, processed, format. For example, a file having a text-based format for storing both a biological sequence (e.g., nucleotide sequence) and its corresponding quality scores (hereafter referred to as a "FASTQ" file) may contain millions of sequence reads. Each of these sequence reads must first be aligned to a reference genome in order to gain any meaning. Therefore, the data file is typically processed by an alignment algorithm (such as Bowtie, BWA, Mosaik, and the like) that considers each read sequentially. As each read is aligned to a reference genome, the alignment algorithm sequentially appends the aligned location to an alignment file, such as a Sequence Alignment and Mapping (SAM) file.

When using cloud computing resources, a provisioned instance may be connected to a networked data store (e.g., using AWS Elastic Block Storage (EBS) or using a networked file system such as NFS, SMB, CIFS, etc.) holding the relevant data. This introduces latency, as access speed is limited by available network bandwidth. Further, this mode of operation is characterized by "bursts" of network activity, in which a primarily CPU-bound application may only request additional data from the network resource once it is needed. This is typically inefficient, as network bandwidth is swamped with the new request and may experience subsequent reductions in speed if other applications also require network resources. There may be long I/O waits for data, leading to occasional crashes of applications.

In some embodiments, the methods and systems described herein provide functionality for stream-processing biomedical data. For example, the methods and systems described herein may provide functionality for solving the problem of processing large amounts of data, such as sequence reads from next-generation sequencing, stored in networked computing resources (such as cloud computing resources). In one of these embodiments, the system may include a file system acting as an intermediary layer between applications making requests to read from and write to files and a storage device (e.g., any type of remote (e.g., cloud-based) backing storage) for data objects hosted by a cloud storage service.

In some embodiments, the methods and systems described herein provide functionality for providing file data on demand based on how fast the file data can be processed by the local machine. The file system may optimize the timing of uploads and downloads based on known or identified patterns of access of common bioinformatics tools. In some embodiments, the file system may not stream at all, depending on how the application is accessing the data. In contrast to a conventional system for processing data that streams on an on-going basis, the present file system intelligently determines whether and when to stream, based on, for example, demand or capacity, as well as potentially applying computation to or transformation of the data as it streams.

Additionally, the methods and systems described herein provide a file system for applications to use (as opposed to a conventional system where data is streamed from one system directly to an application, as in a video on demand system). Furthermore, the present file system may cache, store, and write files that are much larger than the available cache space.

Figure 2:
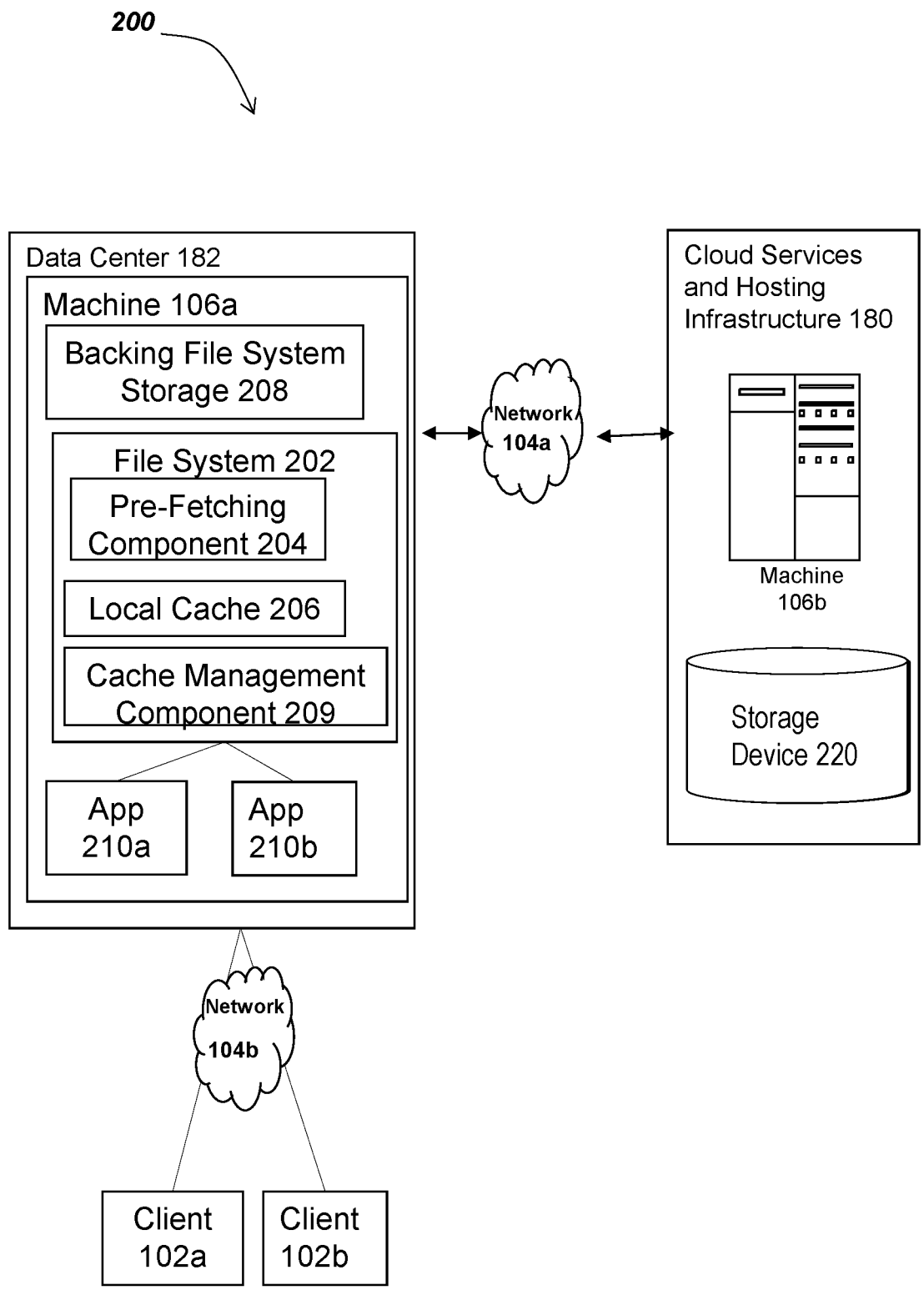
FIG. 2 is a block diagram depicting an embodiment of a system for stream-processing biomedical data.

Referring now to FIG. 2, a block diagram depicts one embodiment of a system for stream-processing biomedical data sets. In brief overview, the system includes a network 104a, a network 104b, a cloud services and hosting infrastructure 180, and a data center 182. For example, an entity in which users perform research on biomedical data may include a data center providing the infrastructure needed to perform that research. In some embodiments, however, the file system 202 executes on a machine 106a that would not be considered part of a data center; that is, the machine 106a executing the file system 202 may be part of any bioinformatics or biomedical data processing environment.

The data center 182 includes a machine 106a executing a file system 202. The file system 202 includes a cache management component 209.

The file system 202 includes a pre-fetching component 204. In one embodiment, the pre-fetching component provides functionality for retrieving, over a network, a portion of a file after determining that a read request is part of a sequential read operation on a file. In another embodiment, the pre-fetching component 204 pre-fetches a portion of a file after receiving two read misses (e.g., after two requested portions of files were determined not to be locally available) in order to confirm that an operation is a sequential read before beginning pre-fetching. This is in contrast to conventional pre-fetching algorithms which are typically used for local applications. Locally hosted data can be read extremely quickly (on the order of microseconds), and thus latency does not cause a bottleneck in file processing. Most applications use simple strategies for pre-fetching local data because optimization is not required to efficiently process local data. In contrast, the file system 202 uses an optimized algorithm to minimize the latency associated with reading non-local data, which is subject to latency on the order of seconds using traditional methods.

The file system 202 includes a local cache 206. In some embodiments, a separate cache is used for both reading and writing operations. In other embodiments, a single cache is used for both reading and writing operations. In one of these embodiments, the file system 202 monitors the kind of file operations being performed and adjust performance for either reading or writing accordingly. In further embodiments, separate caches are used for reading and for writing.

In some embodiments, the file system 202 uses a single cache. In one of these embodiments, the file system 202 allocates multiple larger files ("super blocks") and internally splits the super blocks into multiple portions allocated on the file system 202. By way of example, and without limitation, the super blocks may be a variety of sizes, including 1 Gigabyte chunks. In one embodiment, super blocks can be allocated as required, without limitation. Allocating and dividing super blocks has benefits over alternative methods such as allocating one large region of disk space for all files, or creating a separate block for each file chunk. The former method leaves all files in the one large region susceptible to loss in the potential case of file corruption, and the latter method requires the creation of an unsuitably large number of files.

The machine 106a may further include a backing file system storage 208, which provides local storage for the cache 206. The use of a separate backing file system storage 208 for the cache can be advantageous in that conventional file system operations can be performed using a traditional local file system, such as EXT4, XFS, NTFS, and the like.

The machine 106a may access a machine 106b in the cloud services and hosting infrastructure 180 over a network 104a. The machine 106a may access a storage device 220 in the cloud services and hosting infrastructure 180 over a network 104a. The machine 106a may execute one or more applications 210a-n, each of which may access data stored in the file system 202 (e.g., in the local cache 206). One or more clients 102a-n may access the machine 106a over a network 104b.

In some embodiments, the file system 202 is a software program. In other embodiments, the file system 202 is a hardware module. In still other embodiments, the file system 202 executes on a machine 106a, which may be a machine 100 as described above in connection with FIGS. 1A-1D. The file system 202 may use a pre-fetching component 204 and a local cache 206 to improve performance for common bioinformatics workflows and applications when accessing network resources.

The file system 202 may provide an application programming interface with which the applications may make requests. For example, the file system 202 may be a file system that complies with a Portable Operating System Interface for Unix (POSIX) and support POSIX-based calls from applications, which enables support with bioinformatics tools that are frequently designed to run in a POSIX-compliant architecture.

In some embodiments, the file system 202 obtains a list of files from a file database. The file database may be located on a separate remote machine (e.g., the remote machine 106b of FIG. 1A). The file system 202 communicates with the file database to determine which files should be listed as available in the directory mount point on the machine 106a. One of the benefits of exposing the file database via a POSIX-compliant interface is allowing for the exposure of those files indexed in the file database. Exposing the file database via a POSIX-compliant interface allows users to access files directly and organized in a substantially similar manner as they would be viewed otherwise (e.g., Projects/Folders/Files), which users may leverage to inspect files or do additional work.

In some embodiments, the file system 202 obtains metadata associated with each file from a metadata database. In one embodiment, the metadata database stores various metadata which may be associated with biomedical data files, such as sample type, sequencing technology, read length, and the like.

The file system 202 may also incorporate local caching and pre-fetching, which optimizes performance for file access scenarios common among bioinformatics tools and pipelines; these mechanisms may increase the overall performance of the compute state, and in some cases, are equivalent to accessing files located on a local hard disk. The file system 202 may also preserve the benefits of locally-mounted file systems: content is visible and can be read substantially immediately without the need to move data between instances beforehand. To the end user or application, these features may result in transparent local reads of remote data and transparent writes to the local system that subsequently translate to uploads to remote storage. As will be understood by one of ordinary skill in the art, the file system 202 as described herein is not a conventional file system; rather, it is a file system that has been modified to provide the functionality described herein. The file system 202 may execute in place of a conventional file system. The file system 202 may execute in parallel to a conventional file system.

The storage device 220 may be any type or form of storage unit capable of storing data for use by one or more applications; for example, and without limitation, the storage device 220 may be a database storing bioinformatics data or a storage unit such as an AMAZON SIMPLE STORAGE SERVICE ("S3") "bucket" storing object data remotely (e.g., "in the cloud"). In some embodiments, a machine 106a that is part of a network 104b may access the storage device 220 over a second network 104a; as a result, and as understood by one of ordinary skill in the art, the storage device 220 may be said to be remotely located from the machine 106a (e.g., because the storage device 220 is part of a second network, it is said to be "remote" from the machine 106*a*). Additionally, the storage device 220 may be multiple storage devices, which may further be distributed across multiple cloud services and hosting infrastructures.

As will be understood by those of ordinary skill in the art, conventional storage devices 220 do not typically provide interfaces for engaging with data as if the data were locally stored on a machine 106*a* (e.g., offering only "dumb" services such as bulk file uploads/downloads), rendering files "immutable" or providing only limited disk sizes or problematic concurrent access. In contrast, in some embodiments, use of the methods and systems described herein provide that functionality, resulting in a technological improvement to the machine 106*a* through the use of unconventional technology.

Furthermore, some embodiments of the methods and systems described herein provide functionality allowing workflow processes to begin without needing to download entire files from remote storage first; instead, the file system 202 is mounted and can begin processing data. Some embodiments of the methods and systems described herein provide functionality allowing users and applications to work with files that exceed locally available storage. Further embodiments of the methods and systems described herein provide functionality simplifying hybrid cloud computing environments. For example, in a computing environment (homogeneous or heterogeneous, including, for example, local, cloud, HPC, or various combinations thereof), every instance can mount a drive using the file system 202 to begin processing data. This is particularly useful in situations in which a large set of data files needs to be processed in a distributed fashion.

In some embodiments, the caching and prefetching operations are optimized for bioinformatics tasks and workflow processing.

Figure 3A:
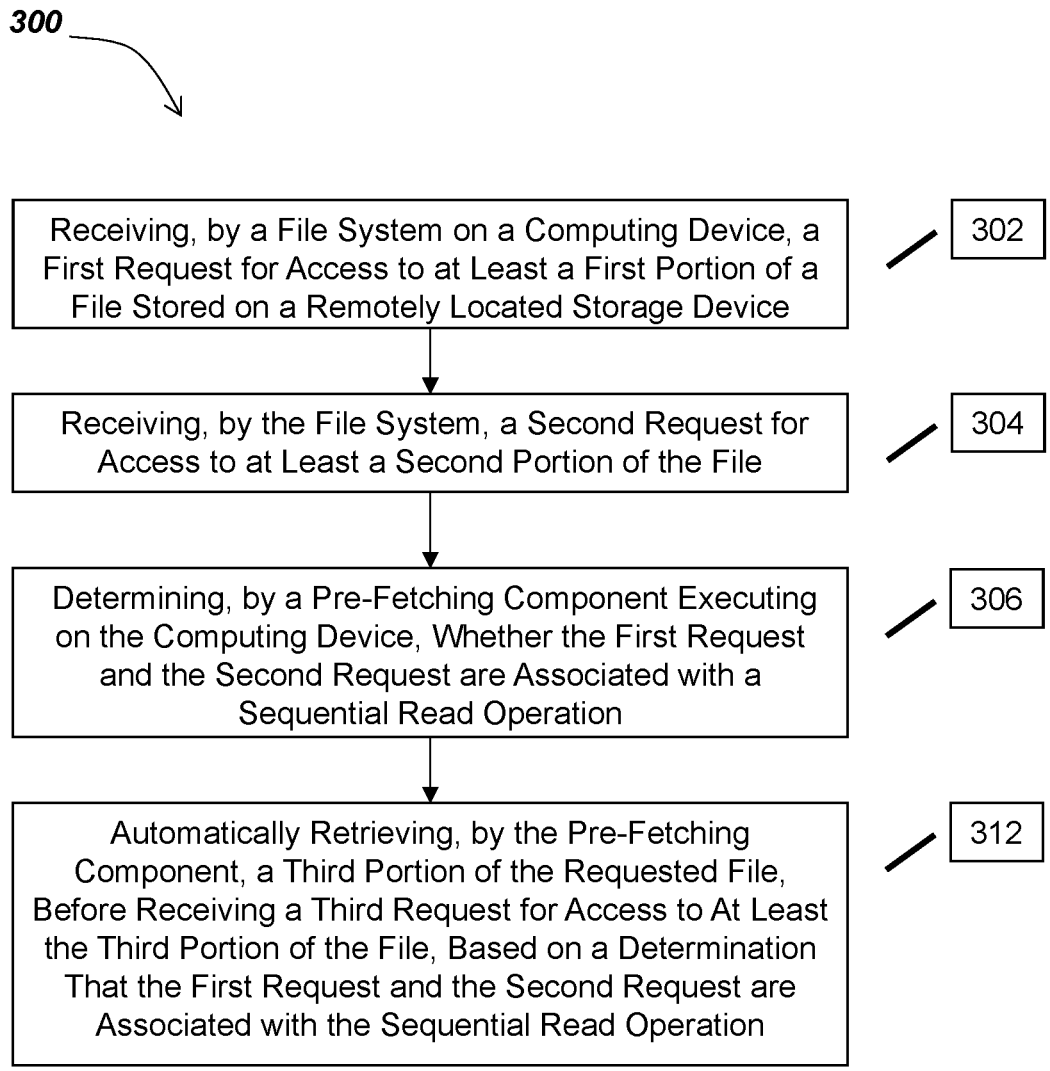
FIG. 3A is a flow diagram depicting one embodiment of a method for stream-processing biomedical data.

Referring now to FIG. 3A, and in brief overview, a flow diagram depicts one embodiment of a method 300 for stream-processing of data, the method 300 including receiving, by a file system on a computing device, a first request for access to at least a portion of a file stored on a remotely located storage device (302). The method 300 includes receiving, by the file system, a second request for access to at least a second portion of the file (304). The method 300 includes determining, by a pre-fetching component executing on the computing device, whether the first request and the second request are associated with a sequential read operation (306). The method 300 includes automatically retrieving, by the pre-fetching component, a third portion of the requested file, before receiving a third request for access to at least the third portion of the file, based on a determination that the first request and the second request are associated with the sequential read operation (312).

Figure 3B:
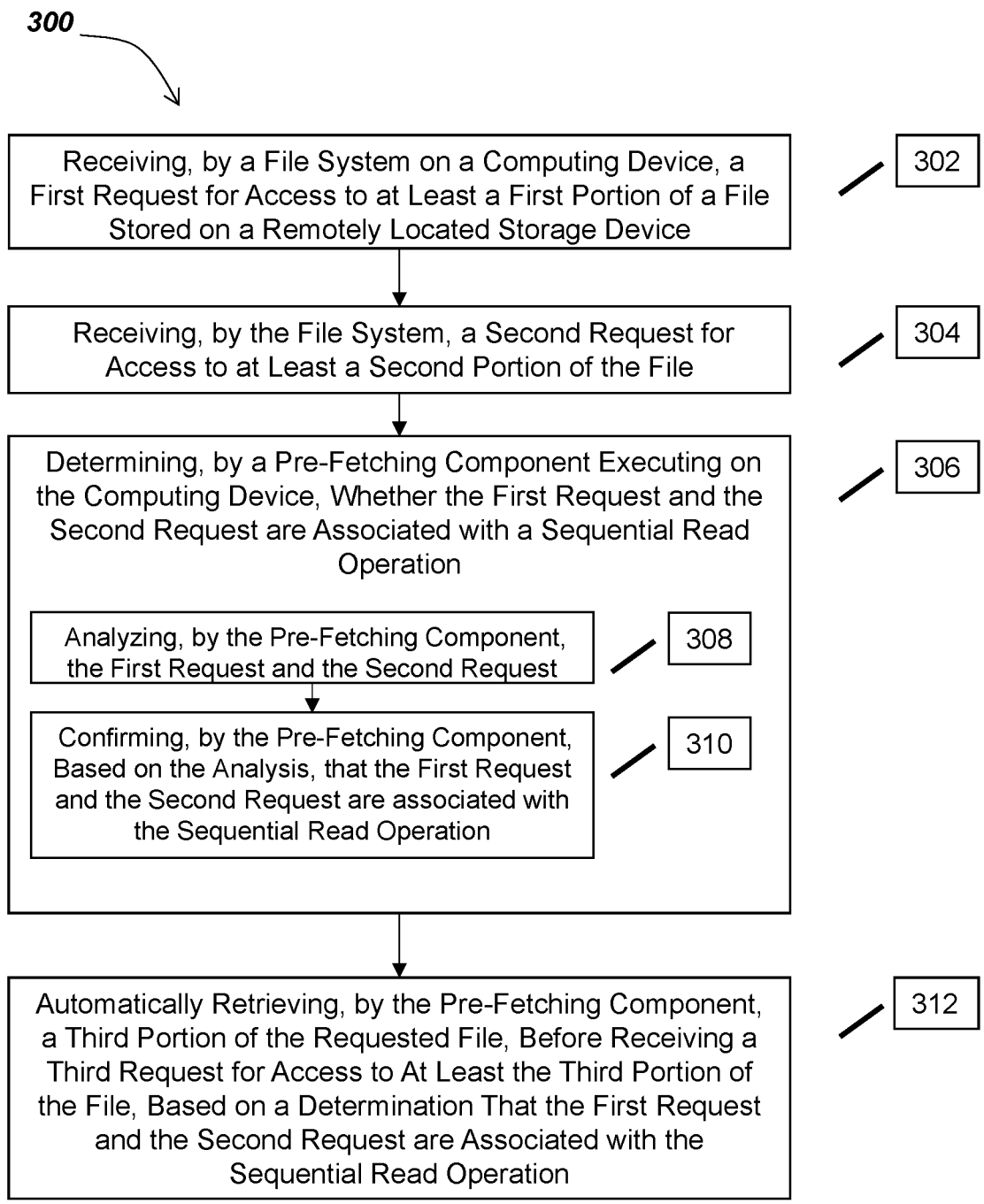
FIG. 3B is a flow diagram depicting one embodiment of a method for stream-processing biomedical data.

Referring now to FIG. 3B, a flow diagram depicts one embodiment of a method 300 for stream-processing biomedical data sets. In brief overview, the method 300 includes receiving, by a file system on a computing device, a first request for access to at least a portion of a file stored on a remotely located storage device (302). The method 300 includes receiving, by the file system, a second request for access to at least a second portion of the file (304). The method 300 includes determining, by a pre-fetching component executing on the computing device, whether the first request and the second request are associated with a sequential read operation (306). Determining whether the first request and the second request are associated with a sequential read operation may further include analyzing, by the pre-fetching component, the first request and the second request (308). Determining whether the first request and the second request are associated with a sequential read operation may further include confirming, by the pre-fetching component, based on the analysis, that the first request and the second request are associated with the sequential read operation (310). The method 300 includes automatically retrieving, by the pre-fetching component, a third portion of the requested file, before receiving a third request for the file (312).

Referring now to FIGS. 3A and 3B in greater detail, and in connection with FIG. 2, the method 300 includes receiving, by a file system on a computing device, a first request for access to at least a portion of a file stored on a remotely located storage device (302). As discussed above, and as will be understood by one of ordinary skill in the art, the request may be a request for a FASTQ file, SAM file, BAM file, files containing biomedical data, or files containing bioinformatics data—for example, any text-based file (e.g., ASCII text), compressed file, or binary file containing an arrangement of characters, symbols, and keywords specifying sequence-related data including, but not limited to, a file or other identifier name, comments, references, associated entries, and an alphanumeric string of characters representing the contents of a DNA, RNA, or protein sequence as generated during a sequencing process.

The file system 202 may receive the request for access to the file from an application 210*a* executing on the computing device 106*a*. The file system 202 may receive the request for access to the file from an end user of the machine 106*a*. The file system 202 may receive the request for access to the file from a client 102*a* in communication with the machine 106*a* over a network 104*b* (e.g., from an application executing on the client 102*a* or from a user of the client 102*a*).

In some embodiments, the system 200 leverages "Filesystem in USErspace" ("FUSE") to provide the file system 202 and its subcomponents with access to requests for files. As will be understood by one of ordinary skill in the art, FUSE is a loadable kernel module that lets non-privileged users create their own file systems without editing kernel code; the user's file system code executes in user space while the FUSE module provides an interface to the kernel interfaces. Within an operating system's kernel, FUSE receives requests from an application (which sent the requests in a conventional manner) and provides those requests to the component that has registered itself as a file system handler for that file (e.g., any file listed as available within the file system mount directory). In one embodiment, the file system 202 has registered itself with an underlying operating system kernel on the machine 106*a* as the file handler for files being requested from the file system mount directory; the file system 202 may then provide requests to the local cache 206 (which may provide the requests to the pre-fetching component 204) or to the pre-fetching component 204. In another embodiment, the local cache 206 registers as the file system handler for files being requested from the file system mount directory.

In some embodiments, the pre-fetching component 204 registers as the file system handler for files being requested from the file system mount directory. The pre-fetching component 204 may determine that at least one portion of the requested file (e.g., the first portion of the requested file) is not stored on the computing device; for example, attempting to process the request may result in a READ_MISS. The pre-fetching component 204 may analyze the request to determine a location of the file. The pre-fetching component 204 may analyze the request to determine a location of the at least one portion of the requested file. For example, the pre-fetching component 204 may determine, based on a file name or a format of the request, that the file is not located on the machine 106a or on a machine or storage device on the network 104b; that is, the pre-fetching component 204 may determine that the request is for a file stored by a remotely-located (e.g., on another network) machine or storage device. The pre-fetching component 204 may analyze a data structure, such as a mapping in an array, to determine a location of the file. The pre-fetching component 204 may retrieve, from the remotely located storage device, the first portion of the requested file. Since the first portion is not being retrieved before the system 200 receives a request for the first portion, one of ordinary skill in the art will understand that the pre-fetching component 204 may include functionality for both fetching and pre-fetching.

The file system 202 may receive a request for only a portion of the file or for the entire file. In some embodiments, in which the request is for an entire file, the file system 202 may translate the request such that only the first few bytes of the file are provided. In some embodiments, file system requests are typically received as an offset and a desired number of bytes. In some embodiments, and as will be understood by one of ordinary skill in the art, reading a file is not an operation to read the entire file, but consists of multiple operations; by way of example, without limitation, a read request may include text such as "READ(file_id, read_offset, max_bytes), where read_offset can be any position in the file, and max_bytes is set by the kernel and/or FUSE. The file system 202 receives such a request and then translates it into a request from the offset that includes a certain chunk (or portion) size. In one embodiment, upon receiving a request for the first read operation, the file system 202 creates a special object or data structure that identifies the size of the file and knows how to translate read operation offset value (which is the position from which the file is being read) to specific chunk number, and offset in that chunk. As an example, if the chunk size is 10, and the file size is 156, the file system 202 would understand the file to have 16 portions. If then a read operation is reading that file with an offset 62, the file system 202 would download part 6, and read that part from offset 2. When the application requesting and reading the data reaches the end of the offset or moves beyond a first portion of a file, a second portion of the file may be downloaded, and the same logic is applied to it.

If the file is small enough to fit within a single chunk (e.g., without limitation, 8 megabytes or other configurable size) then the entire file is accessed and made available in the local cache; however, from the application's perspective, perhaps only the first few bytes are actually read. For larger files, as will be described in greater detail below, the pre-fetching component 204 analyzes the request and, coupled with the file system 202's tracking of the current location within the file, predicts what the application is likely to read next, and then requests the next N portions.

In one embodiment, the cache management component 209 is responsible for efficient management of limited space for caching to handle files much larger than the available cache space while also minimizing read misses. In another embodiment, the cache management component 209 includes logic for determining whether portions of a file are already cached and for triggering the pre-fetching component 204. In some embodiments, downloaded portions of files are cached within the backing file system storage 208. The use of caching enables zero-copy functionality; rather than copying data (e.g., an entire file) to a local instance before working with it, the file system 202 may attach to a given socket and retrieves portions of the file on demand.

In some embodiments, the cache management component 209 creates a data structure that is associated with each file. The data structure may include an array, for example. Each element of the data structure may identify which portions of the file are in the cache (optionally, with pointers). In one embodiment, each file is broken up into a plurality of portions or "chunks." In this embodiment, each element of the data structure may be assigned a unique identifier identifying a location of that chunk. Such data structures are typically created upon receiving a first request to access a portion of a file. Such data structures may further contain information about a file, including a file ID, a size of a single portion (e.g., without limitation, eight megabytes), a length of the file, and a number of portions. The cache management component 209 may use the associated data structure to locate and provide chunks in response to Read/Write operations. Further, the cache management component 209 may call the pre-fetching component 204. In some embodiments, the cache management component 209 calls the pre-fetching component 204 if certain conditions are met.

The method may include determining a location of the first portion of the requested file on the remotely located storage device. In one embodiment, when a read or write request is first received by the file system 202, the request is sent to the cache management component 209, which checks to see if the file is already associated with a data structure; if not, the cache management component 209 creates one and associates it with the file. In another embodiment, the cache management component 209 determines whether the requested data is available by mapping the request for data to the available chunks (e.g., any portions of the file already stored in the local cache 206). For example, if the chunk size is one megabyte and the request ("read_offset" file operation) is for a position 1.5 mb into the file, the cache management component 209 may adjust the "read_offset" parameter to read at 0.5 mb from the second chunk. Note that "read_offset" is not typically larger than the maximum chunk size.

In some embodiments, if the chunk is already in the local cache 206, and it can be read (e.g., resulting in a "READ_HIT"), then the content for that portion of the file is already stored in the local cache 206 and may be provided in response to the request. In one of these embodiments, on READ_HITS, the chunk may be marked as accessed—which may indicate that it is safe to remove the chunk from the cache at a later time, as will be discussed in greater detail below.

The method may include determining, by the cache management component 209, that the first portion of the file is not stored on the computing device 106a. In other embodiments, the chunk is not already in the local cache 206 (e.g., resulting in a "READ_MISS") and will need to be fetched from the storage device 220. The first read request for a file will typically result in a "READ MISS", which instructs the file system 202 to retrieve the requested portion of the file. This is similar to how most file systems store representations of files, in that an internal structure describes where portions of a file are located across the disk. However, in embodiments of the methods and systems described herein, for any given file, most of the data is not available locally. Rather, it is transmitted from a remote source, buffered locally, and expired in a way such that the file system 202 does not exceed the amount of local storage provided, while minimizing latency for an end user. Further, this differs from conventional data streaming services, such as the YOU-TUBE video community provided by Google, Inc., of San Bruno, Calif., since most streaming services allocate the entire file size on disk when receiving a file; in contrast, the file system 202 allocates disk space for only those parts of the file that are needed or being used.

The pre-fetching component 204 may retrieve, from the remotely located storage device, the first portion of the requested file. The pre-fetching component 204 may store the retrieved portion of the requested file in the local cache 206. After download of the portion of the file, the file system 202 proceeds with the read operation.

Cache management may be performed using a data structure, such as a hash table or map, for managing file downloads. This may be the same data structure described above as including an array and listing identifiers for portions of files and corresponding identifiers identifying locations for each of the portions. Alternatively, this may be a separate data structure. Managing the cache using a separate data structure can provide performance improvements. In some embodiments, each portion of a file in the file's associated data structure may be assigned a unique identifier, which can be used to locate the corresponding portion if it is locally available. In another embodiment, the identifier is a unique unsigned 64-bit integer number. The identifier can be used as a "key" to look up the location of the associated chunk in a map (or "hash map"), and can be used as a reference to where the data is stored. If a portion is present locally, the map will indicate its location on disk. In some embodiments, the maps are custom fast integer hash maps. Depending on the programming language used to implement the file system 202, the use of custom maps can provide significant performance improvements. In some embodiments, the data structure of the map is an array of keys and values that is searched using linear probing; when inserting or looking up a given key, the system hashes the key to determine where to begin the search. Concurrent inserts and lookups may be permitted.

In some embodiments, the file system 202 uses a circular search to search the map. For example, if a ' SetItem' or 'GetItem' request reaches the end of the map, the cache management component 209 wraps back around to the beginning (e.g., index 0) and continues searching. As long as the hash table never fills completely, a search finishes either by locating the desired key, or by locating an entry whose key is zero. If the entry is zero, this means that the desired key does not exist in the hash table. This technique may be referred to as open addressing with linear probing, and it may provide a lock-free-friendly hash table technique.

In some embodiments, the requested file may have been divided into one or more portions, or "chunks," of a predetermined size. In other embodiments, the pre-fetching component 204 is configured to request portions of a file of a predetermined size (for example, and without limitation, eight megabytes). The pre-fetching component 204 may use an application programming interface (API) to send the request to the storage device 220 and the API may provide options for requesting file data using an offset and a range of bytes. In some embodiments, a size of a portion of a file and a number of portions to process are selected by an administrator balancing an available local cache size, network bandwidth, and speed of a processing application; for example, by optimizing for use cases related to bioinformatics and genomics applications, such as sequence read alignment. In other embodiments, the system may include dynamic logic that considers the current network throughput speed and overall load to balance with other factors in determining how much data to cache while still maintaining a level of transparency for a user (e.g., an illusion that a file is available in its entirety instead of only a few portions at a time).

Upon retrieving a portion of the requested file, the pre-fetching component 204 may store the retrieved portion in the local cache 206. The local cache 206 may vary in size, based on administrator selections; for example, a cache may vary from a few gigabytes to several terabytes or more. In some instances, the size of the cache may vary based on specific factors such as how many applications are executing concurrently on a particular machine and requesting different files from the file system 202. In one embodiment, the cache is associated with a heap data structure that indexes the locations of presently available data for files visible in a particular directory. In another embodiment, the cache is associated with a map or hash table data structure (e.g., as described above). If a requested portion of a file is not presently available in the local cache 206, the file system 202 may instruct the pre-fetching component to fetch (and, as appropriate, pre-fetch) the requested data. As previously noted, in certain embodiments, the cache may use a local filesystem as backing storage (e.g., the backing file system storage 208).

The pre-fetching component 204 may inform the file system 202 that a portion of the requested file has been successfully retrieved. The file system 202 may respond to the request for the file with an indication that the file is available (although only the portion has been retrieved, not the entire file).

The file system 202 receives a second request for access to at least a second portion of the file (304). In one embodiment, the pre-fetching component 204 retrieves the second portion of the file as described above in connection with retrieval of the first portion of the file. In an embodiment in which the first request is for access to at least a first portion of the file, the second request may be for access to a second portion of the file. Alternatively, the second request may be a second request for the entire file. The pre-fetching component 204 may monitor the requests sent from an application to the kernel to determine whether there is a sequential read operation in progress.

The pre-fetching component 204 determines whether the first request and the second request are associated with a sequential read operation (306). The pre-fetching component 204 may determine that the requestor of the file (e.g., an application 210a, client 102a, or end user) is requesting sequential reading, as opposed to a random request for a particular point in the file. Determining that the requestor is requesting sequential reading is useful when streaming biomedical data due to the speed and quality of reading over typical internet connections, which has much higher latency (e.g., under ~1000 ms for random access) than local reading (e.g., ~20 ms for random access).

Determining whether the first request and the second request are associated with a sequential read operation may include analyzing, by the pre-fetching component, the first request and the second request (308). Analysis may include determining that the second request is for a portion of the file that sequentially follows the first portion. The pre-fetching component 204 may determine that the requestor (e.g., an application) is performing a sequential read operation if the file system 202 receives a request for an initial portion of a file followed by a request for the next sequential portion of the file. For example, the first request may have identified an offset and a request for a certain number of bytes from a file and the second request may have identified the offset and a request for a number of bytes that sequentially follow the number of bytes in the first request.

In the embodiment depicted by FIG. 3B, determining that the first request is for a sequential read operation includes confirming, by the pre-fetching component, based on the analysis, that the first and second requests are associated with the sequential read operation (310).

In some embodiments, the pre-fetching component 204 operates adaptively; that is, if the application is processing data quickly, the pre-fetching component 204 may request and cache additional portions of the file (in addition to the portion or portions that were requested) and, if the application is processing data more slowly, the pre-fetching component 204 may request and cache fewer portions of the file than it might otherwise have pre-fetched. Since this data is not already local, the pre-fetching component 204 may include functionality for addressing network speed, network throughput, as well as the rate of requests in determining whether and how to pre-fetch and cache remotely stored data.

The method 300 includes automatically retrieving, by the pre-fetching component, a third portion of the requested file, before receiving a third request for access to at least the third portion of the file, based on a determination that the first request and the second request are associated with the sequential read operation (312). Having determined that the first request and the second request are for a sequential read operation, the pre-fetching component 204 may proceed to pre-fetch and cache one or more additional portions of the file; for example, in some embodiments, and without limitation, the pre-fetching component 204 may retrieve a pre-determined number of portions of the file (e.g., 30, 40, 60, or any number specified in configuring the pre-fetching component 204). In some embodiments, the pre-fetching component 204 automatically retrieves a fourth portion of the requested file before receiving a fourth request access to at least a fourth portion of a file.

As indicated above, a "READ_MISS" may trigger the cache management component 209 to execute the pre-fetching component 204. In some embodiments, there will be at least two such operations when the application or user initiates reading of a file—the first will result in download of a first chunk and the second will see that a previous chunk for the file is present, resulting in execution of the pre-fetching component 204, which will determine whether the reads are sequential and begin pre-fetching additional components accordingly.

In some embodiments, the pre-fetching component 204 monitors a level of processing applied to a cached portion of a file. For example, the file system 202 may modify the data structure associated with a portion of a file to indicate that if the requestor processes the portion of the file up to that point, the pre-fetching component 204 should retrieve the next sequential portion or portions of the file; for instance, and without limitation, the file system 202 may place a marker at the $20^{th}$ chunk out of 40 chunks and when the file operation accesses the marked chunk from the cache, the pre-fetching component 204 retrieves the next set of 20 chunks from the storage device 220. If on a "READ_HIT," the system encounters a chunk that has previously been tagged, the cache management component 209 may execute the pre-fetching component 204. The ability to pre-fetch in response to a "READ_HIT" for a marked chunk enables continuity when fetching successive sets of chunks. "READ_MISS" operations may also be used to adaptively improve pre-fetching (e.g., by fetching additional file chunks—2, 4, 8, etc., until the system 202 primarily receives READ_HITS).

However, in some embodiments, the pre-fetching component 204 does not retrieve the entire file. In examples in which the file is a genomics file, for example, the file may be very large (in some cases approaching terabytes of data, if not more) and downloading the entire file would potentially overwhelm a conventional cache. By pre-fetching only a subset of the portions of a file, the pre-fetching component 204 also minimizes the likelihood of overloading available network bandwidth.

In one embodiment, the file system 202 has a fixed thread pool for downloading chunks. However, some applications read many files. When this happens, there may be contention for those threads because the file system 202 needs to start downloading lots of different portions of files, which may lead to slowdowns. In some embodiments, the file system 202 resolves this issue by assigning a level of priority to a pre-fetch request; for example, low, medium, or high levels of priority. A custom thread executor provided by the file system 202 may then consider priorities, such that higher priority requests are completed first. Priorities may change over time.

In one embodiment, a "Low" level of priority is assigned to most prefetching requests (e.g., specifying that the file system 202 should complete the request if there are no other higher priority tasks). If a job (e.g., a prefetching request) with low priority fails one or more times, the file system 202 may increase its priority to a "Medium" level of priority. The file system 202 may also decide that prefetching requests can increase to medium priority if the current read operation is getting close to its corresponding chunk location, or if the request has been waiting for some time. (Thus, earlier chunk requests will have higher priority than new chunk requests.) "High" priority may be reserved for any requests resulting from a "READ MISS" on the cache, as this indicates that an application is currently trying to access data; this marks chunks that are required for in-flight operations as high priority. The custom thread executor in the file system 202 ensures that priorities are considered so that higher priority requests are completed first.

In some embodiments, the cache management component 209 includes logic to retrieve parts of files and to expire or "evict" old and unused parts of files from the cache. Eviction processes may be implemented so that the amount of local data managed by the file system does not overwhelm the cache. For example, the cache management component 209 may include functionality for implementing a Least Recently Used (LRU) eviction policy and for applying the LRU policy to both portions of files and entire files. In some embodiments, the use of a separate data structure from the file object (e.g., a hash table or map) to manage caching of chunks is advantageous because the hash table can easily be consulted to determine which chunks to evict.

In some embodiments, the cache management component 209 applies a Last In First Out (LIFO) policy to determine whether to evict a portion of the file; in this way, the cache management component 209 may retain one or more portions of the file (for example, older portions that are likely to be requested again). Retrieved portions of the requested file in the cache may be removed from the local cache. For example, retrieved portions of the requested file in the cache may be removed from the local cache according to a LIFO policy. In some embodiments, the cache management component 209 provides additional functionality for determining whether to evict files when a file is being written. In one of these embodiments, the cache management component 209 may include a custom handler to check whether a least recently used portion of a file (which might otherwise be evicted) is part of a streaming write operation that has not yet completed, in which case the custom handler may prevent the eviction of the portion of the file (e.g., by returning the portion of the file to a cache).

Many bioinformatics workflows operate by transforming data along multiple steps. For example, the output of a first tool is typically processed by a second tool. In one embodiment, the cache management component 209 can optimize caching for such a workflow by using a LIFO eviction process when writing. In this case, the chunks that have most recently been written will be expired first, leaving those chunks at the beginning of the file available. When the write completes (because the tool has finished), then the next tool in the workflow can immediately begin processing that file because its first few sets of chunks have not been expired. The rest of the file can be pre-fetched in the background while the first few sets of chunks are being processed; this may speed up processing time, as it negates or minimizes the need to wait for all parts of a newly written file to upload and be subsequently downloaded from the beginning.

In other embodiments, the cache management component 209 includes a separate data structure (e.g., a hash table or a map) that is optimized for using integer keys and for sorting keys, which allows the system to provide functionality for the creation of custom eviction policies (e.g., not just LRU).

In some embodiments, the cache management component 209 implements a frequency sketch policy, which takes into account the frequency with which a file is used, in addition to how recently the file was used. If a file is used often, it is weighted, rendering it less likely to be evicted from the cache. The model may leverage a probabilistic multiset for estimating a level of popularity of a portion of a file within a time window; the policy may specify a maximum frequency of an element, or an aging process that periodically halves the popularity of all elements, or both.

As an example of one embodiment in which the system implements a frequency sketch policy, a counter matrix may be represented as a single dimensional array holding 16 counters per slot; a fixed depth of four balances the accuracy and cost, resulting in a width of four times the length of the array. To retain an accurate estimation, the array's length equals the maximum number of entries in the cache, increased to the closest power-of-two to exploit more efficient bit masking; this configuration may result in a confidence substantially similar to 93.75% and error bound of e/width. Continuing with this non-limiting example, the frequency of all entries is aged periodically using a sampling window based on the maximum number of entries in the cache. This may be referred to as the reset operation and keeps the sketch fresh by dividing counters by two and subtracting based on the number of odd counters found. The $O(n)$ cost of aging is amortized, ideal for hardware prefetching, and uses inexpensive bit manipulations per array location. A per instance smear may be used to help protect against hash flooding, which would result in the admission policy always rejecting new candidates. The use of a pseudo random hashing function resolves the concern of a denial of service attack by exploiting the hash codes.

As discussed above in connection with the cache management component 209, the system may provide functionality for evicting files or portions of files. In some embodiments, the pre-fetching component 204 includes functionality for removing portions of a file that the local cache 206 has stored for a threshold amount of time; such functionality may be said to "expire" portions of a file. By way of example, in a sequential read operation, an application 210a is likely to process a portion of a file and then move on to the next sequential portion of the file without going back to previous portions; although the file system 202 may allow for maintenance of a plurality of previously-processed portions of files (e.g., keeping a window of available content in the local cache 206), due to the large size of files containing genomic data, retrieving and maintaining too many portions of a file may overload the local cache 206. In some embodiments, markers in the data structure associated with the files are used as indicators of when to expire or "evict" chunks from the local cache 206. For example, the cache management component 209 or the pre-fetching component 204 may reclaim space by 1) removing the oldest file chunks; 2) keeping track of frequency of access and only removing file chunks that are least frequently accessed; and 3) if a chunk is marked as accessed, determining the chunk is safe to remove (especially for sequential read operations).

Therefore, by removing portions of the file stored in the local cache 206 once it is unlikely that a file requestor (e.g., end user or application 210) will access those portions again (e.g., due to the passage of time or the requestor having moved on to process other portions of the file), the file system 202 can provide cached content for the requestor to read, minimizing latency from the requestor perspective, but without requiring retrieval and storage of the entire file. Values of cache sizes may include any number without limitations; for example, and without limitation, 4 gigabytes may work, as well as 20 gigabytes. The size of the local cache 206 may be limited by available local storage (e.g., the backing file system storage 208) and/or the number of concurrent users.

In the event that the pre-fetching component 204 determines that the request is not for a sequential read operation, the pre-fetching component 204 instructs the file system to download requested portions and not perform any additional pre-fetching operations.

In some embodiments, the file system 202 uses locking to manage read requests between potentially conflicting applications. In the context of computing, concurrency refers to the process by which multiple threads of execution run in parallel with one another. Running tasks concurrently significantly enhances the speed and efficiency of execution, but requires safeguards, as conflicts can occur when multiple threads attempt to access or modify a single shared resource. Consider, for example, a situation in which there are multiple, simultaneous attempts to read from or write to a shared hash map data structure. Multiple threads will attempt to access and/or edit the hash map, which can result in an error such as data corruption.

There are several known approaches for preventing conflicts when there are multiple, simultaneous attempts to modify or access shared data. In one embodiment, the file system 202 uses locking to restrict the number of threads that can access a shared data structure (e.g., the hash map) simultaneously. The downside of locking is that, by preventing concurrent access to the data structure, locks can reduce performance. For example, if one lock were used for the entire data structure, only one thread at a time would be able to open/close the lock to access the data structure. In another embodiment, file system 202 uses striped locking—e.g., separate locks for separate parts of the data structure—to avoid the reduction in performance that comes with using a single lock. Simultaneous updates to the same part of the data structure are still restricted, but multiple threads are able to execute concurrently to modify regions of the data structure that do not overlap. For example, the shared hash map data structure is divided into multiple segments, each of which comprises multiple hash keys, and independent segments can be accessed simultaneously by different threads.

Synchronization mechanisms may also be provided inherently in a programming language. In one embodiment, file system 202 uses a built-in version of locking. It is also possible to synchronize data structure access using a lock-free (i.e., non-blocking) mechanism. In one such embodiment, file system 202 uses a lock-free mechanism with "wait-free population oblivious" properties, meaning that the number of operations is bounded and does not depend on the number of active threads. Wait-free operations are guaranteed to complete within a finite number of steps, as opposed to allowing an unbounded number of retries that occur as a result of thread clashes. Using this method, every thread will make progress once it is scheduled to run. In another embodiment, lock-free synchronization mechanisms are combined with a hash map that is not inherently thread-safe.

In some embodiments, the file system 202 also provides functionality for supporting sequential write operations (for example, when an alignment algorithm in an application 210 sequentially outputs a set of aligned sequence reads). In one of these embodiments, the file system 202 provides functionality for caching an instruction to write (e.g., an instruction to modify a portion of a file) and for prioritizing updates such that requests to retrieve (e.g., download) portions of files are processed before instructions to write (e.g., upload modified versions of the portions of files).

In some embodiments, the file system 202 (e.g., via the cache management component 209) implements a customized data structure that allows for concurrent access and modifications, optimized for using integer keys and implementing key sorting. In one of these embodiments, the customized map is a thread-safe map data structure. In another of these embodiments, the customized map includes a wait-free-population-oblivious property for contains(int).

In other embodiments, the cache management component 209 uses three counters and two maps. In one of these embodiments, at any point there are two maps that that should contain the same hashed data elements (both may be of 'Int2ObjectSortedMap' type, for example). In another of these embodiments, only one map is "active" for reading at a time. The first counter serves to control which map is read at a single point, and the other two counters count the number of readers. Once a write operation request comes in, the "inactive" map in the background is modified, the first counter is switched, and when the "inactive" map becomes "active" for reading, the second map is modified. This is designed to save memory and resolve concurrency issues.

Write operations can also benefit from local caching and streaming, including the ability to generate and write to files much larger than available local disk space. Write operations are similar to read operations in that on a first access to a file, a special data structure is created to represent that file. In the case of sequential write operations (also common to bioinformatics tools), once a portion of a file is filled, the file system 202 may commit to uploading that portion of the file once a write operation to the subsequent portion of the file begins. Uploading can also be triggered once a portion of a file is closed or flushed. Once uploading has finished, the file system 202 may mark that chunk such that it may no longer be modified and then may also mark that chunk for expiration.

In some embodiments, the file system 202 may be used for bioinformatics applications executing on specialized compute instances (e.g., either physical or virtual hardware and software); for example, the file system 202 may operate on a compute instance that complies with the requirements of the Health Insurance Portability and Accountability Act (HIPAA). By providing a writeable file system whose pre-fetching and caching functionality is transparent to the end user, the methods and systems described herein satisfy HIPAA requirements. By way of example, the file system 202 may include features that help maintain privacy; for example, only a fraction of data is maintained in the local cache 206. Additionally, some data sets (e.g., those containing genome data) may only be identifiable when stored in their entirety. Additionally, when the file system 202 is unmounted, the data is no longer stored locally. Data could also be stored on a HIPAA compliant S3 bucket and the connection between the S3 bucket and the local instance could be encrypted.

Furthermore, the file system 202 may provide functionality for encrypting the data stored within the local cache 206, securing the path between a bioinformatics application and the accessed data and providing additional security and privacy benefits to users of the system.

One of the benefits of methods and systems implementing the filesystem 202 is that it allows for potentially unlimited storage distributed across a plurality of machines. Each file, or portion of a file, may be located on a separate resource, which can include S3 storage, local or remote disks, and customer-provisioned storage. Because any resource can be used, customers may "attach" their own buckets to an implementation of the file system 202 mount by having the appropriate entries added to the file database. Further, the size of files themselves is potentially unlimited, as different parts of a file may be mapped to separate resources. The potential for unlimited storage allows for storage-intensive tasks (such as joint calling) to be performed using cloud resources. In some embodiments, file locations may be managed by the file database, which acts as a metadata system that provides an API that the filesystem can use to query file locations. The file database in such embodiments acts as a hierarchical network file system that maintains information about files, including their directory locations, owners, date modified, and other data associated with the files. Each entry in the file database may include a pointer to a resource, such as, for example, a particular file located in a particular S3 bucket.

In some embodiments, the methods and systems described herein provide pre-fetching for data used in joint calling operations. As will be understood by one of ordinary skill in the art, joint calling refers to a process of analyzing all variants simultaneously across a sample cohort. Compared to traditional variant calling, joint calling can achieve higher sensitivity for rare variants and variants in low-coverage regions. It can also provide ample information to filter out false positive variant calls. Joint calling is often prohibitively computationally intensive, particularly when scaling to thousands of samples, due to resource limitations related to upload and download times, storage of inputs and outputs, and memory requirements. A joint calling workflow may require the processing of files that, at any given point, surpass the size of any hard disk drive, requiring the provisioning of specialized local computing resources. The computing infrastructure offered by a cloud environment provides scalable resources, yet presently cannot provide resources scaling to the level required by joint calling.

Accordingly, data transfer confers a tremendous burden to joint calling workflows on cloud resources.

Conventional approaches have included batch processing of individual analysis steps and data transfer (e.g., splitting analyses across populations and/or chromosomes), and excluding preprocessing steps such as alignment of sample reads to a reference genome. Such approaches remain hindered by the bottlenecks of data storage and data transfer capabilities. It is neither efficient nor often feasible to copy entire data sets onto computational instances when working with a large sample size. However, systems and methods described herein (including, for example, the file system 202) provide stream read and stream write capabilities that negate or minimize the need for copying entire files. Instead, some embodiments of the systems and methods described herein divide files into portions (or "chunks"), pre-fetch portions into a local cache, process portions successively, and evict portions from the local cache when no longer needed. These mechanisms can increase compute performance to levels comparable to accessing files hosted locally, as the speed of pre-fetching can match that of application execution.

In some embodiments, the methods and systems described herein provide pre-fetching for data used in genotyping a small region of the genome across a large sample cohort. For example, a user may wish to genotype all a plurality of samples for a particular gene or set of genes which are believed to be associated with cancer. If the user believes a particular gene may be related to cancer, he or she may wish to understand all of the variants associated with that gene across all of the patients for which data is available. Analyses such as these can be quite large (e.g., n>10,000) and can quickly consume all of the storage space on a provisioned instance.

Computational workflow processing engines typically divide a workflow (or "task") into a plurality of jobs, and then provision one or more computational instances to process those jobs. If performed on a per-sample basis, this analysis would amount to over 10,000 individual jobs, wherein one job would comprise the processing of one input file (e.g., a Binary Sequence Alignment or BAM file). This is neither a practical nor, in most cases, a feasible use of computational resources. Alternatively, a user may attempt to submit a large number of files to be processed simultaneously. Using traditional methods, this would require that each file be downloaded individually onto a computational instance before processing. As the number of files scales, the amount of time needed to download and copy these files becomes prohibitively large. Additionally, any workflow jobs downstream of this initial job would be unable to begin until all files were processed by the initial job. Further, if only a portion of the BAM file requires analysis (e.g., for just that gene or set of genes), then most of the local storage occupied by the downloaded file is essentially wasted. Accordingly, the number of files that could be processed simultaneously using traditional methods is limited.

In contrast, some embodiments of file systems described herein allow a user to analyze thousands of samples simultaneously in one workflow, without the data transfer limitations that apply to typical workflow processing. Using such a file system, input files are accessed on-demand (e.g., by caching and pre-fetching) and need not be individually downloaded onto a computational instance before a job can begin. Accordingly, jobs can begin processing immediately, resulting in improved processing times of input files (e.g., BAM files) and the efficient use of local storage (e.g., by downloading only data that is needed). In one example, identifying variants in a set of genes for a single BAM file representing aligned sequence reads from a cancer patient's genome can be processed in under 1 minute. Considering that a computational instance can run multiple jobs (i.e., process multiple input files) concurrently, this can amount to the processing of approximately 80 BAM files per minute, representing a significant improvement in the functioning of the computational instance.

In some embodiments, the methods and systems described herein provide pre-fetching for compressed files. For example, a user may wish to process a group of compressed files using a bioinformatics tool that takes individual files as input. Using traditional methods, each of the files would need to first be downloaded onto the computational instance before they can be decompressed in order to be processed by the Bioinformatics tool. Alternatively, a file system as described herein can pre-fetch each of the compressed files and begin decompressing, e.g. by piping the decompressed output directly as input to the bioinformatics tool.

Similarly, in some embodiments, the methods and systems described herein provide pre-fetching for data used in file format conversion. The amount of hard disk space conventionally required to convert files from one format to another (e.g., BAM files to FASTQ files) scales with the number of samples and the number of tasks, potentially rendering the process prohibitively computationally intensive. File systems according to the disclosure negate or minimize the need for large amounts of disk space by pre-fetching portions (or "chunks") of files to be converted, and evicting them from the local cache when processing is complete.

In some embodiments, the methods and systems described herein provide pre-fetching for file metadata or sample IDs. For example, a user may wish to use a bioinformatics tool that does not open or modify input files, but rather groups or arranges input files according to a particular feature such as one or more aspects of metadata. An example of such a tool, available in the Seven Bridges Genomics toolkit SBGTools, is "SBG Pair FASTQs by Metadata." This tool takes a list of FASTQ files as input, accesses and analyzes file metadata, and outputs grouped files according to pairs of paired-end sequence reads. Using traditional methods, the entire list of input files must be copied onto a computational instance in order to be processed. This may be considered a waste of storage and data transfer resources, particularly as the input files do not need to be modified in any way. The file system 202 may therefore negate or minimize the need for copying input files to a computational instance, and instead can pre-fetch the data used to restructure file lists (e.g., sample metadata, sample ID, etc.). Further, file systems as described herein can also provide the needed metadata for a file, as described in further detail below.

In some embodiments, the methods and systems described herein provide pre-fetching for data used in a workflow launching script. As will be understood by one of ordinary skill in the art, a bioinformatics workflow may be launched from a variety of user interfaces such as a command line interface or a graphical user interface provided by a Platform-as-a-Service. A user who wishes to automate a bioinformatics workflow may choose to execute an automation script via a command line interface. However, this requires a certain degree of monitoring on behalf of the user, as the machine executing the automation script must be kept running. An alternative approach is to launch a tool from within a graphical user interface on a Platform-as-a-Service that runs an API script to automate a bioinformatics workflow. This approach can be used to launch multiple workflows, and additionally conveys the benefit of built-in fault tolerance. Conventionally, this approach would require copying all input files associated with the workflow to a selected instance that executes the script, which must be kept running for the duration of the execution of the one or more workflows. File systems as described herein, however, may negate or minimize the need for copying input files onto an instance, and instead pre-fetch the input data required to launch the one or more workflows.

In some embodiments, the file system 202 may incorporate a file database and a metadata database (not shown). The file and metadata databases may be used by a computational engine and means for building and operating workflows, serving as a centralized means for system components to synchronize on content. The file system 202 may use such a file database to discover files to be published as "local" on its file system, and to report any newly created files upstream for general availability by the other system components. The metadata database may include a description of the file (or portions of the file) and its location (or locations), as well as an identification of owners, authorized users, folders, and files. The file system 202 may use such a metadata database to access sets of key-value pairs associated with a file that can identify one or more locations storing one or more portions of data for each file. As most objects in bioinformatics workflows have various metadata associated with them, such as sample type, sequencing technology, read length, etc., the file system 202 offers a mechanism to access this metadata to the platform by creating a "fake".meta file for each file. Other components in the system, such as a computational engine, may then access the .meta file to retrieve metadata; for example, an "example.fastq" file (holding sequence reads in FASTQ format) may have its metadata made available by an "example.fastq.meta" file visible in the same directory.

Therefore, in some embodiments, the methods and systems described herein provide functionality for accessing a distributed file (e.g., a file in which portions of the data that make up the file are stored on a plurality of machines) or files (e.g., in which each file is stored on a different machine in a plurality of machines. In one embodiment, a method for accessing one of a plurality of distributed files includes receiving, by a file system executing on a first computing device, from a metadata database, an identification of at least one file to be published as locally available on the file system. Receiving may include receiving an identification of a folder to be published as locally available. Receiving may include receiving metadata associated with the at least one file. The method may include requesting, by the file system, from the metadata database, an identification of a location storing the file. The method may include receiving, by the file system, from the metadata database, an identification of a second computing device storing the file. The method may include requesting, by the file system, from the second computing device, access to the file. Requesting access may include pre-fetching as described in further detail above.

In another embodiment, a method for accessing a plurality of portions of a file, the plurality of portions stored on a plurality of machines includes receiving, by a file system executing on a first computing device, from a metadata database, an identification of at least one file to be published as locally available on the file system. Receiving includes receiving an identification of a folder to be published as locally available. Receiving includes receiving metadata associated with the at least one file. The method includes requesting, by the file system, from the metadata database, an identification of a location storing a first portion of the file. The method includes receiving, by the file system, from the metadata database, an identification of a second computing device storing the first portion of the file. The method includes requesting, by the file system, from the second computing device, access to the first portion of the file. Requesting access may include pre-fetching as described in further detail above. The method includes requesting, by the file system, from the metadata database, an identification of a location storing a second portion of the file. The method includes receiving, by the file system, from the metadata database, an identification of a third computing device storing the second portion of the file. The method includes requesting, by the file system, from the third computing device, access to the portion of the file. Requesting access may include pre-fetching as described in further detail above.

In such methods for distributed files and portions of files, each file or portion of a file may exist in a different location; however, it appears to be in a single location. Files will be organized in a structure familiar to users of local files (e.g., according to a file structure used for files on a local machine). As noted above, such methods may provide improved methods for joint calling, hybrid cloud computing, and various tasks associated with processing biomedical data.

Although only one file system 202 on one machine 106a has been described, for simplicity and clarity, one of ordinary skill in the art will understand that multiple such machines and systems may be provided. For example, the system 200 may quickly scale to increase a number of file systems 202 executing on one or more machines 106 to support a particular analysis (e.g., including multi-threaded or parallel environments). Additionally, the file system 202 may combine data from multiple storage devices 220 across multiple cloud services and hosting infrastructures 180 automatically and transparently (e.g., without instruction from or depending on an end user), resulting in what appears to the end user to be a single visible file system. In such an embodiment, the file system may leverage semantic groupings of files to present a unified file system to the end user, even though files may actually be stored on a variety of different back-end storage devices across a plurality of hosting infrastructures.

In some embodiments, the methods and systems described herein provide functionality for solving the problem of processing large amounts of biomedical data over a network connection. In one of these embodiments, the functionality performs this in a manner that is transparent to an end user or application, who sees only a local file that can be read substantially immediately, without any need to move data between instances beforehand. The pre-fetching and local caching strategies built into the functionality effectively remove the pre-computation upload, download, and local storage requirements. In some embodiments, the methods and systems described herein provide functionality for working with single files that may be orders of magnitude larger than the amount of space available on a local instance (e.g., FastQ and SAM/BAM alignment files may be 10s or 100s of gigabytes in size). Accordingly, the file system can cache, store, and write files that are much larger than the available local backing storage and/or cache space. Further, because these features are embodied in the file system, no modification or patch is required for applications requesting a file; the pre-fetching and caching components are transparent. In other embodiments, the methods and systems described herein provide functionality for leveraging pre-fetching and caching algorithms that result in high access speeds for files that appear to be locally available; the strategies described allow for two systems—one optimized for processing, and another for storage—to be combined into one.

It should be understood that the systems described above may provide multiple ones of any or each of those components and these components may be provided on either a standalone machine or, in some embodiments, on multiple machines in a distributed system. The phrases 'in one embodiment,' 'in another embodiment,' and the like, generally mean that the particular feature, structure, step, or characteristic following the phrase is included in at least one embodiment of the present disclosure and may be included in more than one embodiment of the present disclosure. Such phrases may, but do not necessarily, refer to the same embodiment.

The systems and methods described above may be implemented as a method, apparatus, or article of manufacture using programming and/or engineering techniques to produce software, firmware, hardware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be LISP, PROLOG, PERL, C, C++, C #, JAVA, or any compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of computer-readable devices, firmware, programmable logic, hardware (e.g., integrated circuit chip; electronic devices; a computer-readable non-volatile storage unit; non-volatile memory, such as semiconductor memory devices, including EPROM, EEPROM, and flash memory devices; magnetic disks such as internal hard disks and removable disks; magneto-optical disks; and CD-ROMs). Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data (including, for example, instructions for tangible storage on non-transitory computer-readable media) from a second computer providing access to the programs via a network transmission line, wireless transmission media, signals propagating through space, radio waves, infrared signals, etc.

Having described certain embodiments of methods and systems for stream-processing biomedical data sets, it will now become apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A method for stream-processing of data, the method comprising:
  receiving, by a file system on a computing device, from an application executing on the computing device, a first request for access to at least a first portion of a file stored on a remotely located storage device;
  receiving, by the file system, a second request for access to at least a second portion of the file;
  determining, by a pre-fetching component of the file system and executing on the computing device, whether the first request and the second request are associated with a sequential read operation; and
  retrieving, by the pre-fetching component, metadata associated with the file and stored in a metadata database, the metadata including at least one key-value pair associated with the file that identifies one or more locations storing one or more portions of data for the file;
  automatically retrieving, by the pre-fetching component, via a network connection to the remotely located storage device, using the metadata, a third portion of the requested file, after receiving the first request and after receiving the second request and before receiving a third request for the third portion of the file, based on a determination, by the pre-fetching component of the file system, that the first request and the second request are associated with the sequential read operation.

2. The method of claim 1 further comprising determining a location of the first portion of the requested file on the remotely located storage device.

3. The method of claim 1 further comprising determining, by a cache management component, that the first portion of the file is not stored on the computing device.

4. The method of claim 3 further comprising retrieving, by the pre-fetching component, from the remotely located storage device, the first portion of the requested file.

5. The method of claim 1, wherein determining further comprises:
  analyzing, by the pre-fetching component, the first request and the second request; and
  confirming, by the pre-fetching component, based on the analysis, that the first request and the second request are associated with the sequential read operation.

6. The method of claim 5, wherein determining that the second request is for a sequential read operation further comprises determining that the second request is for a portion of the file that sequentially follows the first portion.

7. The method of claim 1 further comprising storing, by the pre-fetching component a retrieved portion of the requested file in a cache local to the computing device.

8. The method of claim 7, further comprising removing a retrieved portion of the requested file from the cache.

9. The method of claim 8, wherein retrieved portions of the requested file in the cache are removed according to a Last In, First Out (LIFO) policy.

10. The method of claim 1, further comprising automatically retrieving a fourth portion of the requested file before receiving a fourth request access to at least a fourth portion of a file.

11. A system for stream-processing of data, the system comprising:
a file system on a computing device receiving, from an application executing on the computing device, a first request for access to at least a portion of a file stored on a remotely located storage device and receiving a second request for access to at least a second portion of the file; and
a pre-fetching component of the file system: (i) executing on the computing device, (ii) determining whether the first request and the second request are associated with a sequential read operation, (iii) retrieving metadata associated with the file and stored in a metadata database, the metadata including at least one key-value pair associated with the file that identifies one or more locations storing one or more portions of data for the file, and (iv) automatically retrieving, via a network connection to the remotely located storage device, a third portion of the requested file, after receiving the first request and after receiving the second request and before receiving a third request for the third portion of the file, based on a determination, by the pre-fetching component of the file system that the first request and the second request are associated with the sequential read operation.

12. The system of claim 11, wherein the file is a file containing biomedical data.

13. The system of claim 11, wherein the file system is provided by a kernel module executing in a user space provided by an operating system executing on the computing device.

14. The system of claim 11 further comprising a cache local to the computing device and storing at least one pre-fetched portion of a file.

15. The system of claim 11 further comprising a data structure including an identifier of a portion of the file.

16. The system of claim 11 further comprising a data structure including an identification of a storage location of a portion of the file.

17. A non-transitory, computer-readable medium comprising computer program instructions tangibly stored on the non-transitory computer-readable medium, wherein the instructions are executable by at least one processor to perform a method for stream-processing of data the method comprising:
receiving, by a file system on a computing device, from an application executing on the computing device, a first request for access to at least a first portion of a file stored on a remotely located storage device;
receiving, by a file system on a computing device, a second request for access to at least a second portion of a file stored on the remotely located storage device;
determining, by a pre-fetching component of the file system and executing on the computing device, whether the first request and the second request are associated with a sequential read operation;
retrieving, by the pre-fetching component, metadata associated with the file and stored in a metadata database, the metadata including at least one key-value pair associated with the file that identifies one or more locations storing one or more portions of data for the file; and
automatically retrieving, by the pre-fetching component, using the metadata, via a network connection to the remotely located storage device, a third portion of the requested file, after receiving the first request and after receiving the second request and before receiving a third request for the third portion of the file, based on a determination, by the pre-fetching component of the file system, that the first request and the second request are associated with the sequential read operation.

18. The non-transitory, computer-readable medium of claim 17, wherein determining further comprises:
analyzing, by the pre-fetching component, the first request and the second request; and
confirming, by the pre-fetching component, based on the analysis, that the first request and the second request are associated with the sequential read operation.

* * * * *

UNITED STATES PATENT AND TRADEMARK OFFICE
CERTIFICATE OF CORRECTION

PATENT NO. : 11,558,487 B2
APPLICATION NO. : 17/191187
DATED : January 17, 2023
INVENTOR(S) : Nemanja Zbiljic Page 1 of 1

It is certified that error appears in the above-identified patent and that said Letters Patent is hereby corrected as shown below:

In the Specification

In Column 4, Line 64, delete "display 124" and insert -- display device 124 --, therefor.
In Column 4, Line 66, delete "display 124" and insert -- display device 124 --, therefor.
In Column 6, Line 7, delete "SerialPlus" and insert -- Serial Plus --, therefor.
In Column 6, Line 8, delete "FibreChannel" and insert -- Fibre Channel --, therefor.
In Column 17, Line 39, delete "' SetItem'" and insert -- 'SetItem' --, therefor.
In Column 20, Line 2, delete "the system" and insert -- the file system --, therefor.
In Column 23, Line 43, delete "that that" and insert -- that --, therefor.
In Column 24, Line 27, delete "filesystem" and insert -- file system --, therefor.
In Column 27, Line 42, delete "(e.g.," and insert -- e.g., --, therefor.

Signed and Sealed this
Twenty-first Day of November, 2023

Katherine Kelly Vidal
*Director of the United States Patent and Trademark Office*